United States Patent
Loeker et al.

(10) Patent No.: US 7,842,386 B2
(45) Date of Patent: *Nov. 30, 2010

(54) POWDERY WATER-ABSORBING POLYMERS WITH FINE PARTICLES BOUND BY THERMOPLASTIC ADHESIVES

(75) Inventors: Frank Loeker, Krefeld (DE); Heinz Bremus, Kevelaer (DE); Scott Smith, Greensboro, NC (US)

(73) Assignee: Evonik Stockhausen GmbH, Krefeld (DE)

( * ) Notice: Subject to any disclaimer, the term of this patent is extended or adjusted under 35 U.S.C. 154(b) by 864 days.

This patent is subject to a terminal disclaimer.

(21) Appl. No.: 10/565,770

(22) PCT Filed: Jul. 22, 2004

(86) PCT No.: PCT/EP2004/008184

§ 371 (c)(1),
(2), (4) Date: Sep. 20, 2006

(87) PCT Pub. No.: WO2005/011860

PCT Pub. Date: Feb. 10, 2005

(65) Prior Publication Data

US 2007/0066754 A1    Mar. 22, 2007

(30) Foreign Application Priority Data

Jul. 25, 2003    (DE) ................... 103 34 286

(51) Int. Cl.
*B32B 27/30* (2006.01)
*B32B 27/08* (2006.01)
*C08L 33/02* (2006.01)

(52) U.S. Cl. ............. 428/407; 428/404; 525/127; 525/165

(58) Field of Classification Search ............. 525/165
See application file for complete search history.

(56) References Cited

U.S. PATENT DOCUMENTS

| 4,076,663 | A | 2/1978 | Masuda et al. |
| 4,179,367 | A | 12/1979 | Barthell et al. |
| 4,286,082 | A | 8/1981 | Tsubakimoto et al. |

(Continued)

FOREIGN PATENT DOCUMENTS

AU    6650181 A    7/1981

(Continued)

OTHER PUBLICATIONS

Machine Translation of Eisfeld et al DE 100 26 861.*

(Continued)

*Primary Examiner*—Randy Gulakowski
*Assistant Examiner*—Mike Dollinger
(74) *Attorney, Agent, or Firm*—Smith Moore Leatherwood LLP (57) ABSTRACT

A process for producing and a powdery water-absorbing polymers comprising:
  about 0.01 to 20 wt. % of a fine particle with a particle size of less than about 200 μm;
  about 0.001 to 10 wt. % of a thermoplastic adhesive; and
  about 60 to 99.998 wt. % of a water-absorbing polymer particle with a particle size of about 200 μm and above, wherein the powdery water-absorbing polymers have:
  a flow value (FFC) within the range from about 1 to 13, and/or
  a dust portion of at most about 6 are disclosed.

Also disclosed are a transport process, a composite, chemical products, and a use of a thermoplastic adhesive.

24 Claims, 1 Drawing Sheet

U.S. PATENT DOCUMENTS

| | | |
|---|---|---|
| 4,392,908 A | 7/1983 | Dehnel |
| 4,587,308 A | 5/1986 | Makita et al. |
| 4,693,713 A | 9/1987 | Chmelir et al. |
| 5,002,814 A | 3/1991 | Knack et al. |
| 5,002,986 A | 3/1991 | Fujiura et al. |
| 5,032,628 A | 7/1991 | Choi et al. |
| RE33,839 E | 3/1992 | Chmelir et al. |
| 5,248,709 A | 9/1993 | Brehm |
| 5,368,918 A | 11/1994 | Harada et al. |
| 5,407,442 A | 4/1995 | Karapasha |
| 5,409,771 A | 4/1995 | Dahmen et al. |
| 5,420,218 A | 5/1995 | Toribuchi et al. |
| 5,422,405 A | 6/1995 | Dairoku et al. |
| 5,567,744 A | 10/1996 | Nagata et al. |
| 5,599,335 A | 2/1997 | Goldman et al. |
| 5,599,763 A | 2/1997 | Harada et al. |
| 5,610,220 A | 3/1997 | Klimmek et al. |
| 5,672,419 A * | 9/1997 | Mukaida et al. ............ 442/364 |
| 5,672,633 A | 9/1997 | Brehm et al. |
| 5,712,316 A | 1/1998 | Dahmen et al. |
| 5,716,707 A | 2/1998 | Mukaida et al. |
| 5,731,365 A | 3/1998 | Engelhardt et al. |
| 5,840,321 A | 11/1998 | Engelhardt et al. |
| 5,851,672 A | 12/1998 | Wang et al. |
| 5,859,074 A | 1/1999 | Rezai et al. |
| 5,994,440 A | 11/1999 | Staples et al. |
| 6,027,536 A | 2/2000 | Westerink et al. |
| 6,072,024 A | 6/2000 | Irizato et al. |
| 6,072,101 A | 6/2000 | Beihoffer et al. |
| 6,087,450 A | 7/2000 | Breitbach et al. |
| 6,090,875 A | 7/2000 | Staples et al. |
| 6,124,391 A * | 9/2000 | Sun et al. .................... 524/447 |
| 6,143,821 A | 11/2000 | Houben |
| 6,245,693 B1 | 6/2001 | Gagliardi et al. |
| 6,375,644 B2 | 4/2002 | Mizutani |
| 6,376,011 B1 | 4/2002 | Reeves et al. |
| 6,414,214 B1 | 7/2002 | Engelhardt et al. |
| 6,423,046 B1 | 7/2002 | Fujioka et al. |
| 6,441,266 B1 | 8/2002 | Dyer et al. |
| 6,495,612 B1 | 12/2002 | Corzani et al. |
| 6,498,201 B1 | 12/2002 | Corzani et al. |
| 6,534,561 B1 | 3/2003 | Corzani et al. |
| 6,534,572 B1 | 3/2003 | Ahmed et al. |
| 6,716,514 B2 | 4/2004 | Nissing |
| 6,716,894 B2 | 4/2004 | Kajikawa et al. |
| 6,730,057 B2 | 5/2004 | Zhao et al. |
| 6,867,345 B2 | 3/2005 | Shimoe et al. |
| 6,911,572 B1 | 6/2005 | Bruhn et al. |
| 7,173,086 B2 | 2/2007 | Smith et al. |
| 2001/0049514 A1 | 12/2001 | Dodge, II et al. |
| 2002/0039869 A1 | 4/2002 | Achille |
| 2002/0045869 A1 | 4/2002 | Dodge, II et al. |
| 2002/0090453 A1 | 7/2002 | Muthiah et al. |
| 2003/0012928 A1 | 1/2003 | Malowaniec et al. |
| 2003/0040729 A1 | 2/2003 | Malowaniec et al. |
| 2003/0065296 A1 | 4/2003 | Kaiser et al. |
| 2003/0088220 A1 | 5/2003 | Molander et al. |
| 2003/0093051 A1 | 5/2003 | Malowaniec et al. |
| 2003/0109628 A1 | 6/2003 | Bonfanti et al. |
| 2003/0134552 A1 | 7/2003 | Mehawej et al. |
| 2003/0157318 A1 | 8/2003 | Brehm et al. |
| 2003/0175418 A1 | 9/2003 | Muthiah et al. |
| 2003/0181115 A1 | 9/2003 | Nagasuna et al. |
| 2003/0207639 A1 | 11/2003 | Lin |
| 2004/0054343 A1 | 3/2004 | Barnett et al. |
| 2004/0058159 A1 | 3/2004 | Gagliardi et al. |
| 2004/0071966 A1 | 4/2004 | Inger et al. |
| 2004/0078015 A1 | 4/2004 | Copat et al. |
| 2004/0121681 A1 | 6/2004 | Lindsay et al. |
| 2004/0157989 A1 | 8/2004 | Bruhn et al. |
| 2004/0180998 A1 | 9/2004 | Gonzales et al. |
| 2004/0214499 A1 | 10/2004 | Qin et al. |
| 2004/0222553 A1 | 11/2004 | Desai et al. |
| 2004/0236295 A1 | 11/2004 | Muthiah et al. |
| 2005/0013992 A1 | 1/2005 | Azad et al. |
| 2005/0020780 A1 | 1/2005 | Inger et al. |
| 2005/0043696 A1 | 2/2005 | Schmidt et al. |
| 2005/0065237 A1 | 3/2005 | Schmidt et al. |
| 2005/0096435 A1 | 5/2005 | Smith et al. |
| 2005/0256469 A1 | 11/2005 | Qin et al. |
| 2005/0273067 A1 | 12/2005 | Malowaniec et al. |
| 2006/0289349 A1 | 12/2006 | Hughes |
| 2007/0066754 A1 | 3/2007 | Loeker et al. |
| 2007/0135554 A1 | 6/2007 | McIntosh et al. |

FOREIGN PATENT DOCUMENTS

| | | |
|---|---|---|
| AU | 8744198 A | 4/1999 |
| CA | 2154425 A1 | 1/1996 |
| CA | 2180590 A1 | 1/1997 |
| CA | 2303298 A1 | 3/1999 |
| CA | 2273507 A1 | 12/1999 |
| CA | 2291997 A1 | 6/2000 |
| CA | 2293864 A1 | 6/2000 |
| CA | 2414197 A1 | 1/2002 |
| DE | 2222780 A1 | 11/1973 |
| DE | 2706135 | 8/1978 |
| DE | 3128100 A1 | 1/1983 |
| DE | 3503458 A1 | 8/1985 |
| DE | 3741157 A1 | 6/1987 |
| DE | 3917646 C1 | 8/1990 |
| DE | 4020780 C1 | 8/1991 |
| DE | 4244548 | 7/1994 |
| DE | 4418818 | 1/1995 |
| DE | 4333056 | 3/1995 |
| DE | 19524724 A1 | 1/1997 |
| DE | 19543366 | 5/1997 |
| DE | 19543368 | 5/1997 |
| DE | 19825486 A1 | 2/2000 |
| DE | 19939662 A1 | 2/2001 |
| DE | 10010269 C1 | 7/2001 |
| DE | 10026861 A1 | 12/2001 |
| EP | 0273141 A2 | 7/1988 |
| EP | 0388120 | 9/1990 |
| EP | 0478150 A2 | 4/1992 |
| EP | 0575143 A2 | 12/1993 |
| EP | 0612533 A1 | 8/1994 |
| EP | 0612533 B1 | 8/1994 |
| EP | 0691856 B1 | 1/1996 |
| EP | 0744967 A1 | 12/1996 |
| EP | 827753 A2 | 3/1998 |
| EP | 0850617 A1 | 7/1998 |
| EP | 0888786 A2 | 1/1999 |
| EP | 0963760 A1 | 12/1999 |
| EP | 1164161 A1 | 12/2001 |
| EP | 1179351 A1 | 2/2002 |
| EP | 1259205 A1 | 11/2002 |
| EP | 1259206 A1 | 11/2002 |
| EP | 1259207 A1 | 11/2002 |
| EP | 1350869 A1 | 10/2003 |
| EP | 1354926 A2 | 10/2003 |
| EP | 1359240 A1 | 11/2003 |
| EP | 1402905 A1 | 3/2004 |
| EP | 1433450 A1 | 6/2004 |
| EP | 1503812 A1 | 2/2005 |
| FR | 2838445 A1 | 10/2003 |
| GB | 9011250 DO | 7/1990 |
| JP | 2242858 | 9/1990 |
| JP | 2002/346381 | 12/2002 |
| JP | 2004/298384 | 10/2004 |
| WO | 9118042 | 11/1991 |
| WO | 9511932 A1 | 5/1995 |
| WO | 9614885 A1 | 5/1996 |
| WO | 9845466 A1 | 10/1998 |

| | | |
|---|---|---|
| WO | 9934843 | 7/1999 |
| WO | 9957201 A1 | 11/1999 |
| WO | 0010619 | 3/2000 |
| WO | 0123012 A1 | 4/2001 |
| WO | 0125290 A1 | 4/2001 |
| WO | 0164153 A1 | 9/2001 |
| WO | 0164154 A1 | 9/2001 |
| WO | 0164155 A1 | 9/2001 |
| WO | 0174913 A1 | 10/2001 |
| WO | 03043670 A1 | 5/2003 |
| WO | 03092757 A1 | 11/2003 |
| WO | 03106162 A1 | 12/2003 |
| WO | 2004009683 A1 | 1/2004 |
| WO | 2004018005 A1 | 3/2004 |
| WO | 2004018006 A1 | 3/2004 |
| WO | 2004096301 A2 | 11/2004 |
| WO | 2004098475 A1 | 11/2004 |
| WO | 2005011860 A2 | 2/2005 |
| WO | 2005014067 A1 | 2/2005 |
| WO | 2005014697 A1 | 2/2005 |

OTHER PUBLICATIONS

Chem Crete. Data sheet for AEROSIL 200 silica powder product. Published by Saudi Chem Crete Co. LTD. Available at <http://www.saudichemcrete.com/Cat-11/AERO200.PDF>. Accessed Aug. 12, 2009. p. 1.*

International Search Report mailed on Mar. 2, 2005 in PCT/US2004/035879.

International Search Report mailed on Jun. 11, 2007 in PCT/US2006/061859.

Jacqueline I. Kroschwitz, Concise Encyclopedia of Polmyer Science and Engineering, book, copyright 1990, pp. 213-219, John Wiley & Sons, Inc.

Malcolm P. Stevens, Polymer Chemistry An Introduction, book, copyright, pp. 3-12, Second Edition, Oxford University Press, New York, New York.

Written Opinion of the International Searching Authority mailed on Mar. 2, 2005 in PCT/US2004/035879.

Written Opinion of the International Searching Authority mailed on Jun. 11, 2007 in PCT/US2006/061859.

* cited by examiner

POWDERY WATER-ABSORBING POLYMERS WITH FINE PARTICLES BOUND BY THERMOPLASTIC ADHESIVES

This application is a national stage application under 35 U.S.C. 371 of international application No. PCT/EP2004/008184 filed Jul. 22, 2004, which is based on German Application No. DE 103 34 286.9 filed Jul. 25, 2003, and claims priority thereto.

The present invention relates to powdery water-absorbing polymers, such as superabsorbent polymers, a process for producing powdery water-absorbing polymers, the powdery water-absorbing polymers obtainable by this process, a transport process, a composite, a chemical product, and the use of a thermoplastic adhesive.

Superabsorbent polymers are water-insoluble, cross-linked polymers that are able to absorb and retain under pressure large quantities of water, aqueous liquids, and in particular body liquids, such as urine or blood, by swelling and the formation of hydrogels. Superabsorbent polymers absorb at least 100 times their own weight in water. Further details concerning superabsorbent polymers are disclosed in "Modern Superabsorbent Polymer Technology," F. L. Buchholz, A. T. Graham, Wiley, VCH, 1998. Because of these characteristic properties, these water-absorbing polymers are principally incorporated into sanitary articles, such as for example baby diapers, incontinence products, or sanitary napkins.

Currently, commercially available superabsorbent polymers are substantially cross-linked polyacrylic acids or cross-linked starch-acrylic acid graft polymers, in which the carboxyl groups are partially neutralized with sodium hydroxide or potassium hydroxide. These are attainable by radically polymerizing monomeric acrylic acid or salts thereof in the presence of suitable cross-linking means. In this process, different polymerization processes can be used, such as for example solution polymerization, emulsion polymerization, or suspension polymerization. Finally, water-absorbing polymers are obtained by these different processes in particulate form with a particle diameter within a range from about 150 µm to about 850 µm, which are then incorporated into the sanitary article.

In order to improve the absorption and swelling capacity of these water-absorbing polymer particles, numerous processes have been described in which the surface of the polymer particles is modified. It is, for example, known from DE-A-40 20 780 to convert the water-absorbing polymer particles with alkaline carbonates, which can react with the carboxyl groups of the polymer particles. The surface secondary cross-linking effected in this way leads to an increase of the absorption of the polymer under the action of a pressure.

Besides the conversion of the polymer particles with reactive compounds, in the art numerous processes are also described with which the properties of the water-absorbing polymer particles are achieved by means of a coating with inorganic or organic fine particles.

Thus, in DE-A-35 03 458, it is described that the absorption capacity, the rate of absorption, and the gel stability of superabsorbent polymer particles can be improved by the application of inert inorganic powder materials, such as for example silicon dioxide, in the presence of secondary cross-linking agents. To reduce the hygroscopy and thereby to reduce the caking of the polymer particles, EP-A-0 388 120 proposes the coating of the polymer particles with a porous powder of highly pure silicon dioxide, whereby the powder has an average particle size of about 0.1 µm to about 30 µm and a specific surface of about 500 m²/g.

DE-A-199 39 662 teaches that water-absorbing polymer structures are coated with particulate cyclodextrins and zeolites in order to bind compounds from body liquids which are characterized by an unpleasant odor.

A common problem in all of these processes for subsequent modification is that they lead to a release of fine particles in the form of dust, whereby these fine particles arise through mechanical stress, such as for example by pneumatic conveying and thereupon-contingent abrasion of the water-absorbing polymer particles, or result from a lacking adhesion to the surface of the absorbent fine particles of the inorganic or organic fine particles which are applied for the subsequent modification of the polymer particles.

The release of dust, in particular dust with a particle size of less than about 10 µm, is undesirable for reasons of inhalation toxicity. Fine particles with a particle size of less than about 100 µm cause the visible dust with all its after-effects and lead to handling problems in production and processing distribution. Above all, the flowability of superabsorbent polymers modified at the surface with inorganic or organic particles is negatively influenced by the lack of adhesion of these particles at the surface of the superabsorbent polymer particles.

Embodiments of the present invention overcome the disadvantages arising from the state of the art.

In particular, an embodiment of the present invention comprises providing a process by which it is possible to produce superabsorbent polymer particles modified with inorganic or organic particles, the superabsorbent polymer particles having a sufficient adhesion of the organic or inorganic particles to the surface of the superabsorbent polymer particle.

Another embodiment of the present invention comprises providing water-absorbing particles that have excellent absorption properties, for example with respect to the absorption capacity, the permeability or the speed of absorption, and which have a satisfactory flow behavior in transport in conveyor installations for producing hygiene articles and do not tend to form dust.

Yet another embodiment of the present invention comprises providing water-absorbing polymer particles that have excellent absorption properties, for example with respect to the absorption capacity, the permeability or the speed of absorption, and in addition are characterized by a good mechanical stability.

Additionally, the water-absorbing polymer particles can, in their incorporation into a composite comprising a matrix of a fibrous material, enable a sufficient fixing within the composite by means of adhesion of the water-absorbing polymer particles to the matrix fibers.

It is also an embodiment of the present invention to provide a composite comprising water-absorbing polymer particles, the composite having a water absorption at least comparable with absorbent particles known in the state of the art by means of the excellent absorption properties of the water-absorbing polymer particles or in which a satisfactory fixing of the water-absorbing polymer particles within the composite is achieved, whereby the water-absorbing polymer particles incorporated in the composite have an improved stability and/or a reduced tendency to dust.

One embodiment of the present invention comprises providing chemical products comprising the water-absorbing polymer particles, which products have excellent absorption properties and are characterized by as low as possible a release of dust, for example during mechanical stress.

In addition, an embodiment of the present invention comprises providing a water-absorbing polymer particle which is damaged to as small an extent as possible, and forms as little dust as possible, by the mechanical demands occurring during transport processes in the production of these polymer particles or during the further processing in dosing systems in airlaid machines or diaper machines. Among the above embodiments are included powdery water-absorbing polymers, a process for producing powdery water-absorbing polymers, powdery water-absorbing polymers obtainable by this process, a transport process, a composite, chemical products, and a use of a thermoplastic adhesive.

FIGURE

The foregoing and other features, aspects, and advantages of the present invention will become better understood with regard to the following description, appended claims, and accompanying drawing where:

Powdery water-absorbing polymers according to an embodiment of the present invention comprise:

about 0.01 wt. % to about 20 wt. % in one aspect, in another aspect about 0.05 wt. % to about 15 wt. %, and in yet another aspect about 0.1 wt. % to about 10 wt. % of a fine particle with a particle size determined by sieve analysis of less than about 200 μm in one aspect, in another aspect from less than about 100 μm, and in yet another aspect less than 50 μm;

about 0.001 wt. % to about 10 wt. % in one aspect, in another aspect about 0.01 wt. % to about 5 wt. %, and in yet another aspect about 0.1 wt. % to about 1 wt. % of a thermoplastic adhesive; and about 60 wt. % to about 99.998 wt. % in one aspect, in another aspect about 70 wt. % to about 99 wt. %, and in yet another aspect about 80 wt. % to about 95 wt. % of a water-absorbing polymer particle with a particle size determined by sieve analysis of at least about 200 μm in one aspect, in another aspect of at least about 250 μm, and in yet another aspect of at least about 300 μm, whereby the sum of the above components amounts to about 100 wt. %, wherein the fine particles are bound to the surface of the water-absorbing polymer particle by means of the thermoplastic adhesive and the powdery water-absorbing polymers have either:

a flow value (FFC value) determined according to the test method described herein within the range from about 1 to about 13 in one aspect, in another aspect within the range from about 3 to about 9, and in yet another aspect within the range from about 4 to about 8, and in even yet another aspect within the range from about 5 to about 7, or a dust portion determined according to the test method described herein of at most about 6 in one aspect, in another aspect at most about 4, and in yet another aspect at most about 2.

Powdery water-absorbing polymer particles can have both a flow value (FFC value) and a dust portion in the above-mentioned ranges.

According to an embodiment of the present invention, these fine particles are so-called superabsorbent polymer fine particles that arise during transport or sieving steps during the production and confectioning of superabsorbent polymers.

In a further embodiment of the present invention, the fine particles are not superabsorbent polymers and in particular are not based on water-absorbing, cross-linked, partially neutralized polyacrylic acids or salts thereof. Thus, for example, cyclodextrins are used as fine particles in the confectioning for odor management in hygiene articles, as described in EP 0 691 856 B1.

In an aspect, fine particles that are not based on water-absorbing, cross-linked, partially neutralized polyacrylic acids, or salts thereof can be organic, different from the water-absorbing polymers, or inorganic fine particles.

As organic material, any particulate organic material known to those skilled in the art can comprise part of the powdery water-absorbing polymers according to an embodiment of the present invention, which is commonly used for modifying the properties of water-absorbing polymers. In an aspect, polysaccharides such as cyclodextrins or derivatives thereof can be used as organic fine particles. In another aspect or in addition, cellulose and cellulose derivatives such as carboxymethyl cellulose (CMC), or cellulose ether can be used.

Cyclodextrins or cyclodextrin derivative compounds are disclosed in DE-A-198 25 486 on page 3, line 51 to page 3, line 61. In one aspect, cyclodextrins are non-derivatizated α, β, γ or δ-cyclodextrins. The organic fine particles used can be comprised in the powdery water-absorbing polymers in a quantity in a range from about 0.1 wt. % to about 1 wt. % in one aspect, in another aspect in a quantity within a range from about 0.25 wt. % to about 0.75 wt. %, and in yet another aspect within a range from about 0.4 wt. % to about 0.6 wt. %. The proportions of amounts given in the examples according to an embodiment of the present invention have shown themselves to be particularly advantageous.

As inorganic material, any particulate inorganic material known to those skilled in the art can comprise part of the powdery water-absorbing polymers according to an embodiment of the present invention that is commonly used for modifying the properties of water-absorbing polymers. Silicates, in particular scaffolding silicates such as zeolites or silicates that have been obtained by drying aqueous silicic acid solutions or silica sols belong to an aspect of inorganic fine particles, for example the commercially obtainable products such as precipitation silicic acids and pyrogenic silicic acids, for example aerosols with a particle size within the range of about 5 nm to about 50 nm in one aspect, and in another aspect within the range of about 8 nm to about 20 nm such as "Aerosil 200" from Degussa AG, aluminates, titanium dioxides, zinc oxides, clay materials and further minerals common to those skilled in the art as well as carbon-containing inorganic materials.

Silicates include all natural or synthetic silicates that are disclosed as silicates in "Holleman and Wiberg," Lehrbuch der Anorganischen Chemie, Walter de Gruyter Verlag, 91.-100. Edition, 1985" on pages 750 to 783.

In one aspect, silicates are the zeolites. As zeolites, all synthetic or natural zeolites known to those skilled in the art can be used. Natural zeolites are zeolites from the natrolite groups, the harmotone groups, the modenite groups, the chabasite groups, the faujasite groups (sodalite groups,) or the analcite groups. Examples of natural zeolites are Analcime, Leucite, Pollucite, Wairakite, Bellbergite, Bikitaite, Boggsite, Brewsterite, Chabazite, Willhendersonite, Cowlesite, Dachiardite, Edingtonite, Epistilbite, Erionite, Faujasite, Ferrierite, Amicite, Garronite, Gismondine, Gobbinsite, Gmelinite, Gonnardite, Goosecreekite, Harmotome, Phillipsite, Wellsite, Clinoptilolite, Heulandite, Laumontite, Levyne, Mazzite, Merlinoite, Montesommaite, Mordenite, Mesolite, Natrolite, Scolecite, Offretite, Paranatrolite, Paulingite, Perlialite, Barrerite, Stilbite, Stellerite, Thomsonite, Tschernichite or Yugawaralite. Synthetic zeolites are zeolite A, zeolite X, zeolite Y, zeolite P, or the "ABSCENTS®" products available from UOP LLC.

As zeolites, zeolites of the so-called "medium" ("mittlere") type can be used, in which the $SiO_2/AlO_2$ ratio is smaller than about 10 in one aspect, and in another aspect the $SiO_2/AlO_2$ ratio of these zeolites lies in a range of about 2 to about 10. Besides these "medium" zeolites, zeolites of the "high" ("hohe") type can furthermore be used, to which belong for example the known "molecular sieve" zeolites of the type ZSM, as well as beta-zeolites. These "high" zeolites are characterized by a $SiO_2/AlO_2$ ratio of at least about 35 in one aspect, and in another aspect by a $SiO_2/AlO_2$ ratio in a range of about 200 to about 500.

As aluminates, spinels occurring in nature, in one aspect common spinels, zinc spinel, iron spinal, or chromium spinal are used.

Titanium dioxides can be pure titanium dioxide in the crystal forms rutile, anatase, and brookite, as well as iron-containing titanium dioxides such as for example ilmenite, calcium-containing titanium dioxides such as titanite or perovskite.

Clay materials can be those that are disclosed as clay materials in "Holleman and Wiberg, Lehrbuch der Anorganischen Chemie, Walter De Gruyter Verlag, 91. to 100. Edition, 1985" on pages 783 to 785. In one aspect, clay materials are kaolinite, illite, halloysite, montmorillonite, as well as talc.

Furthermore, the metal salts of mono, oligo- and polyphosphoric acids can be the inorganic fine particles according to an embodiment of the present invention. Among these, in particular the hydrates are one aspect, whereby the mono- to decahydrates and trihydrates are another aspect. As metals, in particular alkali and alkaline earth metals are considered one aspect, whereby alkaline earth metals are another aspect. Among these, Mg and Ca are one aspect and Mg is another aspect. In the context of phosphates, phosphoric acids, and metal compounds thereof, reference is made to "Holleman and Wiberg, Lehrbuch der Anorganischen Chemie, Walter De Gruyter Verlag, 91. to 100. Edition, 1985" on pages 651 to 669.

In one aspect, carbon-containing, but non-organic materials, are those pure carbons which are mentioned as graphites in "Holleman and Wiberg, Lehrbuch der Anorganischen Chemie, Walter De Gruyter Verlag, 91. to 100. Edition, 1985" on pages 705 to 708. In another aspect, graphites are artificial graphites such as for example coke, pyrolytic graphite, active carbon, or soot.

The fine particles comprising part of the powdery water-absorbing polymers according to an embodiment of the present invention can be present in the form of fibers, foams, or particles, whereby fibers and particles are one aspect and particles are another aspect. If organic polysaccharides, such as for example cellulose fine particles, are used as fine particles in one aspect, then in another aspect the fine particles are used in the form of fibers. These fibers can have a linear density within the range of about 0.5 to about 6 in one aspect and in another aspect within the range of about 0.7 to about 4 detex. Further details of suitable fibers are disclosed in EP-A-0 273 141.

In the use of organic or inorganic fine particles or of mixtures thereof described in the following, these fine particles can comprise part of the powdery water-absorbing polymers in a quantity within a range of about 0.1 wt. % to about 1 wt. % in one aspect, in another aspect in a quantity within a range from about 0.25 wt. % to about 0.75 wt. %, and in yet another aspect within a range from about 0.4 wt. % to about 0.6 wt. %. The proportions given in the examples according to embodiments of the present invention have shown themselves as particularly advantageous, in particular for the above-detailed organic and inorganic individual compounds.

In an embodiment according to the present invention, the powdery water-absorbing polymers comprise as a component a mixture of an organic and an inorganic fine particle.

In an embodiment of the powdery water-absorbing polymer according to the present invention, the fine particle that is, in an aspect, not based on water-absorbing cross-linked poly(meth)acrylates comprises, to at least about 80 wt. % in one aspect, in another aspect to at least about 90 wt. %, and in yet another aspect to at least about 95 wt. %, based on the weight of the fine particle which is, in another aspect, not based on water-absorbing cross-linked poly(meth)acrylates, an inorganic fine particle.

In another embodiment of the powdery water-absorbing polymer according to the present invention, the fine particle which is, in an aspect, not based on water-absorbing cross-linked poly(meth)acrylates comprises, to at least about 80 wt. % in one aspect, in another aspect to at least about 90 wt. %, and in yet another aspect to at least about 95 wt. %, based on the weight of the fine particle which is, in another aspect, not based on water-absorbing cross-linked poly(meth)acrylates, an organic fine particle.

It is furthermore an embodiment according to the present invention that the fine particles which are, in an aspect, not based on water-absorbing, cross-linked, partially neutralized polyacrylic acids or salts thereof have a specific surface determined according to the BET method within a range of about 30 $m^2/g$ to about 850 $m^2/g$ in one aspect, in another aspect within a range of about 40 $m^2/g$ to about 500 $m^2/g$, in yet another aspect within a range of about 100 $m^2/g$ to about 300 $m^2/g$ $m^2/g$, and in even yet another aspect within a range from about 150 $m^2/g$ to about 250 $m^2/g$. In general, and in the case that the fine particles are sipernates and aerosols, the specific surface lies within a range of about 30 $m^2/g$ to about 850 $m^2/g$ in one aspect, in another aspect within a range from about 40 $m^2/g$ to about 500 $m^2/g$, and in yet another aspect within a range from about 100 $m^2/g$ to about 300 $m^2/g$, and is determined with nitrogen in an area meter according to ISO 5794, Annex D. In an embodiment of the powdery water-absorbing polymer according to the present invention, at least about 90 wt. % in one aspect, in another aspect at least about 95 wt. %, and in yet another aspect at least about 99 wt. % of the fine particles which are, in an aspect, not based on water-absorbing cross-linked polyacrylates a particle size of less than about 200 µm in one aspect, in another aspect of less than about 100 µm, and in yet another aspect of less than about 1 µm, and in even yet another aspect of less than about 500 nm, and in even yet a further aspect of less than about 100 nm. The sipernates have a particle size within the range of about 10 µm to about 180 µm in one aspect, in another aspect within the range of about 20 µm to about 150 µm, and in yet another aspect within the range of about 30 µm to about 110 µm. The particle size can be determined according to ASTM C 690-1992 with a Multisizer. In another embodiment of the present invention, the sipernates have a mean particle size within the range of about 1 µm to about 40 µm in one aspect, in another aspect within the range of about 2 µm to about 30 µm, and in yet another aspect within the range of about 3 µm to about 20 µm as determined according to ASTM C 690-1992.

A "thermoplastic adhesive" is understood according to embodiments of the present invention to be a material that has no adhesive properties below a given temperature. Above a given temperature, in one aspect above the melting point of the material, the material shows sticky properties or adhesive properties, whereby these properties also remain in the solidified state after binding two substrates in the molten state. The respective sticky or adhesive properties can appear at least about 10° C. in one aspect, in another aspect at least about 20° C., and in yet another aspect within a range of about 21° C. to about 100° C. above the melting point, determined by differential scanning calometry (DSC), of the material or material mixture used as thermoplastic adhesive. It is also possible in the present invention to use thermoplastic adhesives that comprise two or more different compounds. The two or more compounds can differ from each other in the chemical composition or in their molecular weight or in both.

The thermoplastic adhesives can be used as particles. In one aspect, at least about 50 wt. % and in another aspect at least about 70 wt. % of the particles have a particle size within the range of about 10 μm to about 500 μm in one aspect, in another aspect about 25 μm to about 250 μm, and in yet another aspect about 40 μm to about 120 μm. The particle sizes can be determined by sieve analysis up to a size of about 20 μm. For particle sizes of less than about 20 μm, light scattering can be used to determine the particle size.

As thermoplastic adhesives, polymeric materials with a molecular weight of more than about 1000 g/mol that have a corresponding melting temperature and at a corresponding application temperature do not decompose or show any alteration of the molecular composition which would otherwise be disadvantageous for the adhesive effect are generally suitable.

The number average molecular weight ($M_n$) determined by gel permeation chromatography (GPC) of the polymers that can be used as thermoplastic adhesives lies between about 10,000 g/mol and about 1,000,000 g/mol in one aspect, in another aspect between about 20,000 g/mol and about 300,000 g/mol and in yet another aspect between about 50,000 g/mol and about 150,000 g/mol.

The molecular weight distribution of the cited polymers, which can likewise be determined by gel permeation chromatography (GPC), can be monomodal. Optionally, a polymer usable as thermoplastic adhesive can also have a bi-modal or higher-modal distribution.

Compounds that can be used as thermoplastic adhesives according to embodiments of the present invention comprise a portion of at least about 60 wt. % in one aspect, in another aspect a portion of about 80 wt. %, and in yet another aspect a portion of about 100 wt. %, based on the total weight of the thermoplastic adhesive, a melting temperature according to ISO 11357 of at least about 50° C. in one aspect, in another aspect at least about 60° C., and in yet another aspect at least about 70° C., whereby a melting temperature according to ISO 11357 of about 300° C. in one aspect, in another aspect about 250° C., and in yet another aspect 200° C. is not exceeded.

The thermoplastic adhesives that can be used according to embodiments of the present invention can be not only solid but also can have a non-sticky surface, at temperatures of up to about 30° C. in one aspect, and in another aspect at temperatures lying there above, for example at up to about 40° C. or up to about 50° C.

At a little above the melting temperature, the thermoplastic adhesive can have relatively low viscosity. In one aspect, its melt viscosity according to Brookfield (ASTM E 28) with a number 27 spindle at a temperature of about 160° C. should be less than 2,000 Pas in one aspect, in another aspect smaller than 1,200 Pas, and in yet another aspect smaller than 600 Pas.

A thermoplastic adhesive according to embodiments of the present invention can be a material that comprises at least about 10 wt. % in one aspect, in another aspect at least about 50 wt. %, and in yet another aspect at least about 90 wt. %, based on the total weight of the thermoplastic adhesive, a polymer selected from polyurethanes, polyesters, polyamides, polyolefins, polyvinyl esters, polyethers, polystyrenes, polyimides, in particular polyether imides, sulfur polymers, in particular polysulfones, polyacetals, in particular polyoxymethylene, fluoride plastics, in particular polyvinylidine fluoride, styrene-olefin copolymers, polyacrylates or ethylene-vinyl acetate copolymers or mixtures of two or more of the cited polymers, whereby among these polymers, polycondensates and among these polyesters are an aspect.

Polyurethanes according to embodiments of the present invention are understood to be all polymers that have at least two urethane groups in the polymer backbone.

In embodiments according to the present invention, all thermoplastic polyurethanes known to those skilled in the art in the area of polyurethane chemistry are suitable, in particular such polyurethanes as are used commonly in the production of thermoplastic formed bodies, in particular of films, or for thermoplastic coating of surfaces. For example, polyester polyurethanes or polyether polyurethanes are suitable, as are obtainable by conversion of dicarboxylic acids with corresponding polyfunctional alcohols, in particular difunctional alcohols, for example difunctional polyethers such as polyethylene oxide, to polyether- or polyester polyols and then conversion of the corresponding polyether- or polyester polyols with di- or polyfunctional isocyanates. In one aspect, thermoplastic polyurethanes are those polyurethanes which are distributed by the company Kern GmbH, Großmeischeid, Germany, under the product code "TPU D," "TPU 93 A," "TPU 80 A" and "TPU GF 20." In another aspect, a thermoplastic polyurethane is the polyurethane with the product number "6005" distributed by the company Schaetti AG, Zurich, Switzerland under the product code "SchaettiFix®."

Polyester, according to embodiments of the present invention, are understood to be all polymers that have at least two ester groups and no urethane groups in the polymer backbone. In the present invention, all thermoplastic polyesters known to those skilled in the art are suitable, in particular such polyesters as are commonly used in the production of thermoplastic formed bodies, in particular of films, or for thermoplastic coating of surfaces. For example, polyesters are suitable, as obtainable by conversion of dicarboxylic acids with corresponding polyfunctional alcohols, in particular difunctional alcohols, for example difunctional polyethers such as polyethylene oxide. In one aspect, polyesters can be composed of terephthalic acid or a derivative thereof, isophthalic acid or a derivative thereof, adipinic acid or isophthalic acid or a derivative thereof, adipinic acid or a derivative thereof, and at least one polyol, such as butanediol or ethylene glycol or mixtures thereof. An embodiment of the ester comprises terephthalic acid or a derivative thereof, isophthalic acid, or a derivative thereof, or mixtures thereof in a quantity within the range of about 30 wt. % to about 80 wt. % in one aspect, and in another aspect in a quantity within the range of about 40 wt. % to about 65 wt. %. A further embodiment of the ester comprises adipinic acid or a derivative thereof in a quantity within the range of about 3 wt. % to about 20 wt. % in one aspect, and in another aspect in a quantity within the range from about 5 wt. % to about 15 wt. %. Furthermore, another embodiment of the ester comprises at least one polyol, in one aspect butanediol or ethylene glycol or a mixture thereof, in a quantity within the range of about 25 wt. % to about 55 wt. % in one aspect, and in another aspect in a quantity within the range of about 30 wt. % to about 40 wt. %. The above wt. % amounts are always based on the respective ester.

In one aspect, thermoplastic polyesters are those polyesters that are distributed by the company Kern GmbH, Großmaischeid, Germany, under the product codes "PET," "PBT," "PBT V 0," "PC," "PC V 0," "PC FDA," "PC GF 10 V0 " and "PC GF 30." In another aspect are those thermoplastic polyesters which are distributed by the company Schaetti AG, Zurich, Switzerland, under the product code "SchaettiFix" under the product numbers "373," "374," "376," "386," "386 F," and "399." In yet another aspect are the thermoplastic copolyesters which are distributed by the company Degussa AG, Düsseldorf, Germany, under the product codes "Dynacoll 7000," "Dynacoll 7380," "Dynacoll 7340," "Vestamelt 4280," "Vestamelt 4481," "Vestamelt 4580," and "Vestamelt 4680/4681."

In embodiments according of the present invention, suitable polyamides include all plastic polyamides obtainable by conversion of suitable di- or polycarboxylic acids with corresponding amines. In an embodiment of the present invention, polyamides are used that were at least partially produced by using dimeric fatty acids as dicarboxylic acids. In a further embodiment of the present invention, nylon types are used as melt adhesive, for example, nylon-6,6, nylon-6,9 or nylon-6, 12.

In one aspect, thermoplastic polyamides are those polyamides that are distributed by the company Kern GmbH, Großmaischeid, Germany under the product codes "PA 6 E," "PA 6," "PA 6 flex," "PA 6 V 0," "PA 6 MoS2," "PA 6 M 30," "PA 6 M 30 V 0," "PA 6 G 210," "PA 6 G 210 H," "PA 6 G 212," "PA 6 G 216," "PA 6 G 210 Öl," "PA 6 G 210 AX," "PA 6 G 210 MoS2," "PA 6 G 210 AX," "PA 66 E," "PA 66," "PA 66H," "PA 66 PE," "PA 6/6T," "PA 12 E," "PA 12," and "PA 12 G." In another aspect are those thermoplastic polyamides that are distributed by the company Schaetti AG, Zurich, Switzerland under the product code "SchaettiFix®" and the product numbers "5018," "5047," "5045," "5005," "5000," "5010," and "5065." In yet another aspect, polyamides are thermoplastic polyamides that are distributed by the company Degussa AG, Düsseldorf, Germany under the product codes "Vestamelt 171," "Vestamelt 250," "Vestamelt 251," "Vestamelt 253," "Vestamelt 350," "Vestamelt 351," "Vestamelt 353," "Vestamelt 430," "Vestamelt 432," "Vestamelt 450," "Vestamelt 451," "Vestamelt 470," "Vestamelt 471," "Vestamelt 640," "Vestamelt 722," "Vestamelt 730," "Vestamelt 732," "Vestamelt 733," "Vestamelt 742," "Vestamelt 750," "Vestamelt 753," "Vestamelt 755," "Vestamelt 840," "Vestamelt X 1301," "Vestamelt 3041," "Vestamelt 3261," "Vestamelt X 4685," "Vestamelt X 7079," and "Vestamelt X 1010."

Suitable polyolefins according to an embodiment of the present invention are for example obtainable by radical or coordinative polymerization of alpha-olefins, in particular of ethylene or propylene. In embodiments of the present invention, both homopolymers and copolymers are suitable for use as thermoplastic adhesive. If copolymers are used as thermoplastic adhesive, then in an aspect such thermoplastic adhesives can comprise at least a portion of atactic copolymers, in another aspect, however, substantially comprise atactic copolymers. For producing corresponding compounds, suitable processes are known to those skilled in the art.

In one aspect, thermoplastic polyolefins are those polyethylenes and polypropylenes that are distributed by the company Kern GmbH, Großmaischeid, Germany, under the product codes "PE UHMW," "PE HMW," "PE HMW ELS," "PE HD," "PE LD," "PP-H," "PP-C," "PP-C HI," "PP V2," "PP M20" and "PP M40." In another aspect, thermoplastic polyolefins are those thermoplastic ethylenes that are distributed by the company Schaetti AG, Zurich, Switzerland under the product code "SchaettiFix®" and the product numbers "1800," "1820," "1822," "1825," "120" and "140."

In an embodiment of the present invention, polymers and copolymers of vinyl acetates are suitable as polyvinyl ester. In another embodiment according to the present invention, copolymers of vinyl acetate with alpha-olefins, in particular with ethylene, are used. In one aspect, the copolymers have a vinyl acetate content of about 15 wt. % to about 40 wt. %, and in another aspect about 18 wt. % to about 25 wt. %. The melt index of polymers of this type in one aspect lies at about 150 to about 500, measured according to ASTM D 1238.

In one aspect, thermoplastic polyvinyl esters are those polyvinyl esters which are distributed by the company Schaetti AG, Zurich, Switzerland under the product code "SchaettiFix®" and the product numbers "2047," "2048," "1303," and "2050."

In an embodiment of the present invention, suitable polyethers include, for example, polyethylene oxide, polypropylene oxide, polybutylene oxide, or polytetrahydrofuran, in particular with a molecular weight of greater than about 5,000.

Suitable polystyrenes, for example, include polymers of styrene or α-methylstyrene.

Likewise in an aspect, suitable polymers for the thermoplastic adhesives include styrene-olefin block copolymers, as obtainable by copolymerization of styrene with mono- or diolefins, in an aspect butadiene. In another aspect, suitable in this context includes the polymers referred to as synthetic rubbers, as are obtainable from the copolymerization of styrene and butadiene or styrene and isoprene. Likewise suited in embodiment of the present invention are synthetic rubbers of the cited type, which have been subjected to a partial or full hydration. Synthetic rubbers usable as thermoplastic adhesives in the present invention in one aspect have a number average molecular weight of about 70,000 to about 200,000, for example about 80,000 to about 150,000.

In one aspect, thermoplastic polymers based on styrene include those styrene polymers that are distributed by the company Kern GmbH, Großmaischeid, Germany under the product codes "PS," "PS V2," "SB," "SB V0," "SB ELS," "ABS," "ABS V0," "ABS EMV," "SAN," "ASA," and "ASA HI."

The terms "polyacrylate" or "polyacrylates," as used in the present text, in the context of the thermoplastic adhesive, refer in the following both to polymers or copolymers of acrylic acid and/or its derivatives, and to polymers or copolymers of methacrylic acid and/or its derivatives.

Polyacrylates can be produced, in that acrylic acid and/or methacrylic acid and/or derivatives of acrylic acid and/or methacrylic acid, for example esters thereof with mono- or polyfunctional alcohols, alone or as a mixture of two or more thereof, are polymerized in known ways, for example radically or ionically.

In an embodiment of the present invention, thermoplastic adhesive based on polyacrylates, homopolymers, or copolymers that have, besides the acrylic acid esters (acrylates) additionally styrene, acrylonitrile, vinyl acetate, vinyl propionate, vinyl chloride, vinylidene chloride, ethylene, propylene, and/or butadiene, can be used.

As monomer, in the production of thermoplastic adhesives based on polyacrylates, include in particular methacrylate, ethyl acrylate, n-butylacrylate, isobutyl acrylate, tert-butylacrylate, hexylacrylate, 2-ethyl-hexylacrylate, or laurylacrylate. Optionally, as further monomers, additionally acrylic acid, methacrylic acid, acrylamide, or methacrylamide can be added in small quantities during the polymerization.

Optionally, yet further acrylates and/or methacrylates with one or more functional groups can be present during the polymerization. For example, these are maleic acid, itaconic acid, butanediol diacrylate, hexanediol diacrylate, triethylene glycol diacrylate, tetraethylene glycol diacrylate, neopentyl glycol diacrylate, trimethylolpropane triacrylate, 2-hydroxyethylacrylate, 2-hydroxyethylmethacrylate, hydroxypropyl acrylate, propylene glycol methacrylate, butanediol monoacrylate, ethyl diglycol acrylate, as well as sulfonic acid group-carrying monomers, for example 2-acrylamido-2-methyl propane sulfonic acid. In one aspect are acrylic ester vinyl ester copolymers, acrylic ester styrene copolymers, or acrylic ester methacrylic ester copolymers.

In a further embodiment, powdery, water-absorbing polymers according to the present invention, copolymers of acrylic acid and styrene are comprised part of the thermoplastic adhesive based on polyacrylates, whereby the monomer ratio in melt adhesives of this type amounts to about 70:30 (styrene:acrylic acid).

The thermoplastic adhesives comprising part of the powdery water-absorbing polymers according to embodiments of the present invention comprise at least one of the above compounds. It is, in embodiments of the present invention, however, also possible that the thermoplastic adhesives used comprise two or more of the cited compounds.

In yet another embodiment of the present invention, the thermoplastic adhesive comprises at least two polymers selected from the group consisting of vinyl acetate homo polymers, vinyl acetate copolymers, poly-alpha-olefins, polyacrylates, polymethacrylates, polyacrylic acid esters, polymethacrylic acid esters, polyethers, polyesters, polyamides or polyurethanes.

Besides one or more of the above-mentioned polymers, a thermoplastic adhesive, comprising part of the powdery water-absorbing polymers according to an embodiment of the present invention, can comprise yet further additives that allow a modification of the adhesive properties. For example, the so-called tackifier-resins are suitable for this purpose, which can be sub-divided into natural resins and synthetic resins (artificial resins). Suitable tackifier-resins are, for example, alkyd resins, epoxide resins, melamine resins, phenol resins, urethane resins, hydrocarbon resins, as well as natural resins from colophony, wood turpentine, and tall oil. As synthetic hydrocarbon resins, for example ketone resins, coumarone-indene resins, isocyanate resins, and terpene-phenol resins are suitable. In embodiments of the present invention, synthetic resins are an aspect.

Resins of this type can comprise part of the thermoplastic adhesives comprising part of the powdery water-absorbing polymers according to an embodiment of the present invention in a quantity of up to about 50 wt. % in one aspect, in another aspect up to about 60 wt. %, and in yet another aspect up to about 70 wt. %, based on the thermoplastic adhesive, for example in a quantity of about 0.1 wt. % to about 35 wt. % in one aspect, or about 3 wt. % to about 20 wt. % in another aspect.

Besides the already mentioned components, a thermoplastic adhesive, comprising part of the powdery water-absorbing polymers according to an embodiment of the present invention, can additionally comprise at least one wax. A "wax," in embodiments of the present invention, is understood as a water-insoluble compound or a mixture of two or more of such compounds with a melting point of about 90° C. to about 165° C. Suitable waxes include, for example, paraffin waxes, polyethylene waxes, polypropylene waxes, montan waxes, Fischer-Tropsch waxes, microcrystalline waxes, or carnauba waxes.

Waxes of this type can be present in a thermoplastic adhesive, as can be used in embodiment of the present invention, in a quantity of up to about 60 wt. % in one aspect, in another aspect up to about 70 wt. %, and in yet another aspect up to about 80 wt. %, based on the thermoplastic adhesive, for example in a quantity of about 5 wt. % to about 60 wt. %. If compounds are used in embodiments of the present invention as thermoplastic adhesives, which are obtainable from the polymerization of alpha-olefins, the portion of waxes in melt adhesives of this type amounts to at least about 5 wt. % in one aspect or at least about 10 wt. % in another aspect.

An aspect in a design of embodiments of the present invention can be that the thermoplastic adhesive is applied to the powdery water-absorbing polymer as a liquid phase. For this purpose, besides solutions of the thermoplastic adhesive, emulsions and dispersions are suitable. As solvents for this liquid phase, all organic and inorganic solvents known to those skilled in the art are considered suitable. The liquid phases comprise the thermoplastic adhesive in a quantity within the range of about 0.001 wt. % to about 50 wt. % in one aspect, in another aspect within a range of about 0.01 wt. % to about 25 wt. %, and in yet another aspect within the range of about 0.1 wt. % to about 15 wt. %, based on the solvent quantity. Also, the liquid phase comprises as solvent to at least about 60 wt. % in one aspect, and in another aspect to at least about 80 wt. % water. Additionally, the liquid phase has at least one of the following described secondary cross-linkers, whereby in this context secondary cross-linker quantities are within a range of about 0.001 wt. % to about 20 wt. % in one aspect, and within a range of about 0.01 wt. % to about 10 wt. % in another aspect.

Among the above-disclosed thermoplastic adhesives, sulfonated thermoplastic adhesives are particularly suitable for use in liquid phases. Among these, sulfonated polyesters, sulfonated polyamides such as nylon are one aspect. A further group of thermoplastic adhesives suitable for liquid phases are polyethoxylated polyamides such as nylon, for example obtainable as Lurotex® from BASF AG in Ludwigshafen. Additionally suitable for use in liquid phases are styrene acrylic acid copolymers such as Joncryl® from SC Johnson, block copolymers comprising polyurethane and polyethylene oxide blocks, at least partially hydrolysed ethylene vinyl acetate copolymers, and emulsions comprising polyacrylate and polyesters.

In an embodiment relating to powdery water-absorbing polymers according to the present invention, the water-absorbing polymer particles comprising part of the polymers are based on:

($\alpha$1) about 0.1 wt. % to about 99.999 wt. % in one aspect, in another aspect about 20 wt. % to about 98.99 wt. %, and in yet another aspect about 30 wt. % to about 98.95 wt. % of polymerized, ethylenically unsaturated, acidic group-containing monomers or salts thereof, or polymerized, ethylenically unsaturated monomers containing a protonated or a quaternary nitrogen, or mixtures thereof, wherein mixtures comprising at least ethylenically unsaturated, acidic groups-containing monomers, preferably acrylic acid, are an aspect;

($\alpha$2) 0 to about 70 wt. % in one aspect, in another aspect about 1 wt. % to about 60 wt. %, and in yet another aspect about 1 wt. % to about 40 wt. % of polymerized, ethylenically unsaturated monomers which can be co-polymerized with ($\alpha$1);

($\alpha$3) about 0.001 wt. % to about 10 wt. % in one aspect, in another aspect about 0.01 wt. % to about 7 wt. %, and in yet another aspect about 0.05 wt. % to about 5 wt. % of one or more cross-linkers;

(α4) 0 wt. % to about 30 wt. % in one aspect, in another aspect about 1 wt. % to about 20 wt. %, and in yet another aspect about 5 wt. % to about 10 wt. % of water-soluble polymers; and (α5) 0 wt. % to about 20 wt. % in one aspect, in another aspect about 0.01 wt. % to about 7 wt. %, and in yet another aspect about 0.05 wt. % to about 5 wt. % of one or more auxiliaries, wherein the sum of the component weights (α1) to (α5) amounts to about 100 wt. %.

Monoethylenically unsaturated, acid group-containing monomers (α1) can be partially or fully, in one aspect partially neutralized. The monoethylenically unsaturated, acid group-containing monomers can be neutralized to at least about 25 mol. % in one aspect, in another aspect to at least about 50 mol. %, and in yet another aspect to about 50 mol. % to about 90 mol. %. The neutralization of the monomers (α1) can occur before and also after the polymerization. Further, the neutralization can occur with alkali metal hydroxides, alkaline earth metal hydroxides, ammonia, and carbonates and bicarbonates. In addition, every further base is conceivable that forms a water-soluble salt with the acid. A mixed neutralization with different bases is also conceivable. Neutralization with ammonia or with alkali metal hydroxides is one aspect, and another aspect is with sodium hydroxide or with ammonia.

Furthermore, in a polymer, free acid groups can predominate, so that this polymer has a pH value lying in the acid range. This acidic water-absorbing polymer may be at least partially neutralized by a polymer containing free basic groups, in one aspect amine groups, that is basic compared to the acidic polymer. These polymers are termed "mixed-bed ion-exchange absorbent polymers" (MBIEA polymers) in the literature and are disclosed in, inter alia, WO 99/34843. As a rule, MBIEA polymers represent a composition that contains on the one hand basic polymers that are able to exchange anions, and on the other hand contains a polymer that is acidic compared to the basic polymer and that is able to exchange cations. The basic polymer contains basic groups and is typically obtained by the polymerization of monomers that carry basic groups or groups that can be converted into basic groups. These monomers are in particular those that contain primary, secondary, or tertiary amines or the corresponding phosphines or at least two of the aforementioned functional groups. This group of monomers includes in particular ethyleneamine, allylamine, diallylamine, 4-aminobutene, alkyloxycycline, vinylformamide, 5-aminopentene, carbodiimide, formaldacin, melamin and the like, as well as their secondary or tertiary amine derivatives.

In one aspect, monoethylenically unsaturated, acidic group-containing monomers (α1) include acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbinic acid, α-chlorosorbinic acid, 2'-methylisocrotonic acid, cinnamic acid, p-chlorocinnamic acid, β-stearic acid, itaconic acid, citraconic acid, mesaconic acid, glutaconic acid, aconitic acid, maleic acid, fumaric acid, tricarboxythylene, and maleic acid anhydride, wherein acrylic acid and methacrylic acid are one aspect and acrylic acid another aspect.

Besides these carboxylate group-containing monomers, in another aspect monoethylenically unsaturated acidic group-containing monomers (α1) include ethylenically unsaturated sulfonic acid monomers or ethylenically unsaturated phosphonic acid monomers.

In one aspect, ethylenically unsaturated sulfonic acid monomers include allylsulfonic acid or aliphatic or aromatic vinylsulfonic acids or acrylic or methacrylic acids. Aliphatic or aromatic vinylsulfonic acids can be vinylsulfonic acid, 4-vinylbenzylsulfonic acid, vinyltoluenesulfonic acid, and styrenesulfonic acid. Acrylic or methacrylic acids can be sulfoethyl(meth)acrylate, sulfopropyl(meth)acrylate, and 2-hydroxy-3-methacryloxypropylsulfonic acid. As (meth)acrylamidoalkylsulfonic acid, 2-acrylamido-2-methylpropanesulfonic acid is an aspect.

In another aspect, ethylenically unsaturated phosphonic acid monomers include, for example, vinylphosphonic acid, allylphosphonic acid, vinylbenzylphosphonic acid, (meth)acrylamidoalkylphosphonic acids, acrylamidoalkyldiphosphonic acids, phosphonomethylated vinylamines, and (meth)acrylphosphonic acid derivatives.

According to embodiments of the present invention, the water-absorbing polymer can comprise at least about 50 wt. % in one aspect, in another aspect at least about 70 wt. %, and in yet another aspect at least about 90 wt. % carboxylate group-containing monomers. Also, according to embodiments of the present invention, the water-absorbing polymer can comprise at least about 50 wt. % in one aspect, and in another aspect at least about 70 wt. % acrylic acid, which is neutralized preferably to at least about 20 mol. % in one aspect, and in another aspect to at least about 50 mol. %.

In one aspect, ethylenically unsaturated monomers (α1) containing a protonated nitrogen can be dialkylaminoalkyl(meth)acrylates in the protonated form, for example dimethylaminoethyl(meth)acrylate hydrochloride or dimethylaminoethyl(meth)acrylate hydrosulfate, as well as dialkylaminoalkyl(meth)acrylamides in the protonated form, for example dimethylaminoethyl(meth)acrylamide hydrochloride, dimethylaminopropyl(meth)acrylamide hydrochloride, dimethylaminopropyl(meth)acrylamide hydrosulfate, or dimethylaminoethyl(meth)acrylamide hydrosulfate.

In one aspect, ethylenically unsaturated monomers (α1) containing a quaternated nitrogen are dialkylammoniumalkyl(meth)acrylates in quaternated form, for example trimethylammoniumethyl(meth)acrylate-methosulfate or dimethylethylammoniumethyl(meth)acrylate-ethosulfate as well as (meth)acrylamidoalkyldialkylamine in quaternated form, for example (meth)acrylamidopropyltrimethylammonium chloride, trimethylammoniumethyl(meth)acrylate chloride, or (meth)acrylamidopropyltrimethylammonium sulfate.

In one aspect, monoethylenically unsaturated monomers (α2) which can be co-polymerized with (α1) are acrylamides and (meth)acrylamides.

Possible (meth)acrylamides besides acrylamide and methacrylamide include alkyl-substituted (meth)acrylamides or aminoalkyl-substituted derivatives of (meth)acrylamide such as N-methylol(meth)acrylamide, N,N-dimethylamino(meth)acrylamide, dimethyl(meth)acrylamide, or diethyl(meth)acrylamide. Possible vinylamides are for example N-vinylamides, N-vinylformamides, N-vinylacetamides, N-vinyl-N-methylacetamides, N-vinyl-N-methylformamides, vinylpyrrolidone. Among these monomers, acrylamide is one aspect.

Furthermore, monoethylenically unsaturated monomers (α2) that are copolymerizable with (α1) can be monomers that are dispersible in water. Monomers that are dispersible in water can be acrylic acid esters and methacrylic acid esters, such as methyl(meth)acrylate, ethyl(meth)acrylate, propyl(meth)acrylate, or butyl(meth)acrylate, as well as vinyl acetate, styrene, and isobutylene.

In one aspect, cross-linkers (α3) according to the present invention include compounds that have at least two ethylenically unsaturated groups in one molecule (cross-linker class I), compounds that have at least two functional groups that can react with functional groups of the monomers (α1) or (α2) in a condensation reaction (=condensation cross-linkers), in an addition reaction or a ring-opening reaction (cross-linker class II), compounds which have at least one ethylenically unsaturated group and at least one functional group which can react with functional groups of the monomers (α1) or (α2) in a condensation reaction, an addition reaction or a ring-opening reaction (cross-linker class III), or polyvalent metal cations (cross-linker class IV). Thus, with the compounds of cross-linker class I, a cross-linking of the polymer is achieved by radical polymerization of the ethylenically unsaturated groups of the cross-linker molecules with the monoethylenically unsaturated monomers (α1) or (α2), while with the compounds of cross-linker class II and the polyvalent metal cations of cross-linker class IV, a cross-linking of the polymer is achieved respectively via condensation reaction of the functional groups (cross-linker class II) or via electrostatic interaction of the polyvalent metal cation (cross-linker class IV) with the functional groups of the monomer (α1) or (α2). With compounds of cross-linker class III, a cross-linking of the polymers is achieved correspondingly by radical polymerization of the ethylenically unsaturated groups or also by condensation reaction between the functional groups of the cross-linkers and the functional groups of the monomers (α1) or (α2).

In one aspect, compounds of cross-linker class I include poly(meth)acrylic acid esters, which have been obtained for example by conversion of a polyol, such as for example ethylene glycol, propylene glycol, trimethylolpropane, 1,6-hexanediol, glycerine, pentaerythritol, polyethyleneglycol, or polypropyleneglycol, of an aminoalcohol, a polyalkylenepolyamine, such as for example diethylenetriamine or triethylenetetraamine, or of an alkoxidized polyol with acrylic acid or methacrylic acid. In another aspect, compounds of cross-linker class I include polyvinyl compounds, poly(meth)allyl compounds, (meth)acrylic acid esters of a monovinyl compound or (meth)acrylic acid esters of a mono(meth)allyl compound, such as the mono(meth)allyl compounds of a polyol or of an aminoalcohol. In this context, DE 195 43 366 and DE 195 43 368 are referred to.

Examples of compounds of cross-linker class I include alkenyldi(meth)acrylates, for example ethyleneglycoldi(meth)acrylate, 1,3-propyleneglycoldi(meth)acrylate, 1,4-butyleneglycoldi(meth)acrylate, 1,3-butyleneglycoldi(meth)acrylate, 1,6-hexanedioldi(meth)acrylate, 1,10-decanedioldi(meth)acrylate, 1,12-dodecanedioldi(meth)acrylate, 1,18-octadecanedioldi(meth)acrylate, cyclopentanedioldi(meth)acrylate, neopentylglycoldi(meth)acrylate, methylenedi(meth)acrylate or pentaerythritoldi(meth)acrylate, alkenyldi(meth)acrylamides, for example N-methyldi(meth)acrylamide, N,N'-3-methyldutylidenebis(meth)acrylamide, N,N'-(1,2-dihydroxyethylene)bis(meth)acrylamide, N,N'-hexamethylenebis(meth)acrylamide or N,N'-methylenebis(meth)acrylamide, polyalkoxydi(meth)acrylates, for example diethyleneglycoldi(meth)acrylate, triethyleneglycoldi(meth)acrylate, tetraethyleneglycoldi(meth)acrylate, dipropyleneglycoldi(meth)acrylate, tripropyleneglycoldi(meth)acrylate or tetrapropyleneglycoldi(meth)acrylate, bisphenol-A-di(meth)acrylate, ethoxylated bisphenol-A-di(meth)acrylate, benzylidenedi(meth)acrylate, 1,3-di(meth)acryloyloxypropanol-2, hydroquinonedi(meth)acrylate, di(meth)acrylate esters of trimethylolpropane which is alkoxylated in one aspect, an in another aspect ethoxylated, preferably with about 1 to about 30 mol alkylene oxide per hydroxyl group, thioethyleneglycoldi(meth)acrylate, thiopropyleneglycoldi(meth)acrylate, thiopolyethyleneglycoldi(meth)acrylate, thiopolypropyleneglycoldi(meth)acrylate, divinyl ethers, for example 1,4-butanedioldivinyl ether, divinyl esters, for example divinyl adipate, alkanedienes, for example butadiene or 1,6-hexadiene, divinylbenzene, di(meth)allyl compounds, for example di(meth)allyl phthalate or di(meth)allyl succinate, homo- and co-polymers of di(meth)allyldimethylammonium chloride and homo- and co-polymers of diethyl(meth)allylaminomethyl(meth)acrylateammonium chloride, vinyl(meth)acrylic compounds, for example vinyl(meth)acrylate, (meth)allyl(meth)acrylic compounds, for example (meth)allyl(meth)acrylate, (meth)allyl(meth)acrylate ethoxylated with about 1 mol to about 30 mol ethylene oxide per hydroxyl group, di(meth)allyl esters of polycarboxylic acids, for example di(meth)allyl maleate, di(meth)allyl fumarate, di(meth)allyl succinate or di(meth)allyl terephthalate, compounds with about 3 or more ethylenically unsaturated, radically polymerizable groups such as for example glycerine tri(meth)acrylate, (meth)acrylate esters of glycerine ethoxylated with preferably about 1 mol to about 30 mol ethylene oxide per hydroxyl group, trimethylolpropanetri(meth)acrylate, tri(meth)acrylate esters of trimethylolpropane which is alkoxylated in one aspect, an in another aspect ethoxylated, preferably with about 1 mol to about 30 mol alkylene oxide per hydroxide group, trimethacrylamide, (meth)allylidenedi(meth)acrylate, 3-allyloxy-1,2-propanedioldi(meth)acrylate, tri(meth)allylcyanurate, tri(meth)allylisocyanurate, pentaerythritoltetra(meth)acrylate, pentaerythritoltri(meth)acrylate, (meth)acrylic acid esters of pentaerythritol which is ethoxylated in one aspect with about 1 mol to about 30 mol ethylene oxide per hydroxyl group, tris(2-hydroxyethyl)isocyanuratetri(meth)acrylate, trivinyltrimellitate, tri(meth)allylamine, di(meth)allylalkylamines, for example di(meth)allylmethylamine, tri(meth)allylphosphate, tetra(meth)allylethylenediamine, poly(meth)allyl ester, tetra(meth)allyloxyethane, or tetra(meth)allylammonium halides.

Compounds of cross-linker class II can be compounds that have at least two functional groups that can react in a condensation reaction (=condensation cross-linkers), in an addition reaction or in a ring opening reaction with the functional groups of the monomers (α1) or (α2) in one aspect, and in another aspect with acidic groups of the monomers (α1). These functional groups of the compounds of cross-linker class II can be alcohol, amine, aldehyde, glycidic, isocyanate, carbonate, or epichloro functions.

Examples of compounds of cross-linker class II include polyols, for example ethylene glycol, polyethylene glycols such as diethylene glycol, triethylene glycol, and tetraethylene glycol, propylene glycol, polypropylene glycols such as dipropylene glycol, tripropylene glycol, or tetrapropylene glycol, 1,3-butanediol, 1,4-butanediol, 1,5-pentanediol, 2,4-pentanediol, 1,6-hexanediol, 2,5-hexanediol, glycerine, polyglycerine, trimethylolpropane, polyoxypropylene, oxyethylene-oxypropylene block copolymers, sorbitan-fatty acid esters, polyoxyethylene sorbitan-fatty acid esters, pentaerythritol, polyvinylalcohol and sorbitol, aminoalcohols, for example ethanolamine, diethanolamine, triethanolamine or propanolamine, polyamine compounds, for example ethylenediamine, diethylenetriamine, triethylenetetraamine, tetraethylenepentaamine or pentaethylenehexaamine, polyglycidyl ether compounds such as ethyleneglycoldiglycidyl ether, polyethyleneglycoldiglycidyl ether, glycerinediglycidyl ether, glycerinepolyglycidyl ether, pentaerithritolpolyglycidyl ether, propyleneglycoldiglycidyl ether, polypropyleneglycoldiglycidyl ether, neopentylglycoldiglycidyl ether, hexanediolglycidyl ether, trimethylolpropanepolyglycidyl ether, sorbitolpolyglycidyl ether, phthalic acid diglycidyl ester, adipinic acid diglycidyl ether, 1,4-phenylenebis(2-oxazoline), glycidol, polyisocyanates, in one aspect diisocyanates such as 2,4-toluenediioscyanate and hexamethylenediisocyanate, polyaziridine compounds such as 2,2-bishydroxymethylbutanol-tris[3-(1-aziridinyl)propionate], 1,6-hexamethylenediethylene urea and diphenylmethane-bis-4,4'-N,N'-diethylene urea, halogen epoxides for example epichloro- and epibromohydrin and α-methylepichlorohydrin, alkylene carbonates such as 1,3-dioxolane-2-one (ethylene carbonate), 4-methyl-1,3-dioxolane-2-one (propylene carbonate), 4,5-dimethyl-1,3-dioxolane-2-one, 4,4-dimethyl-1,3-dioxolane-2-one, 4-ethyl-1,3-dioxolane-2-one, 4-hydroxymethyl-1,1-dioxolane-2-one, 1,3-dioxane-2-one, 4-methyl-1,3-dioxane-2-one, 4,6-dimethyl-1,3-dioxane-2- one, 1,3-dioxolane-2-one, poly-1,3-dioxolane-2-on, polyquaternary amines such as condensation products from dimethylamines and epichlorohydrin. Further compounds of the cross-linker class II are polyoxazolines such as 1,2-ethylenebisoxazoline, cross-linkers with silane groups such as γ-glycidoxypropyltrimethoxysilane and γ-aminopropyltrimethoxysilane, oxazolidinones such as 2-oxazolidinone, bis- and poly-2-oxazolidinone and diglycolsilicates.

In one aspect, compounds of cross-linker class III include hydroxyl or amino group-containing esters of (meth)acrylic acid, such as for example 2-hydroxyethyl (meth)acrylate, as well as hydroxyl or amino group-containing (meth)acrylamides, or mono(meth)allylic compounds of diols.

The polyvalent metal cations of cross-linker class IV are derived in one aspect from singly or multiply charged cations, the singly charged in particular from alkali metals such as potassium, sodium, or lithium, wherein lithium is one aspect. In another aspect, doubly charged cations are derived from zinc, beryllium, or alkaline earth metals such as magnesium, calcium, strontium, wherein magnesium is one aspect. Further cations applicable according to an embodiment of the present invention, with higher charge, include cations from aluminium, iron, chromium, manganese, titanium, zirconium, and other transition metals as well as double salts of such cations or mixtures of the named salts. The use of aluminium salts and alums and various hydrates thereof such as e.g. $AlCl_3 \cdot 6\ H_2O$, $NaAl(SO_4)_2 \cdot 12\ H_2O$, $KAl(SO_4)_2 \cdot 12\ H_2O$ or $Al_2(SO_4)_3 \cdot 14\text{-}18\ H_2O$ is one aspect.

The use of $Al_2(SO_4)_3$ and its hydrates as cross-linkers of the cross-linker class IV is another aspect.

Water-absorbing polymers can be those which are cross-linked by cross-linkers of the following cross-linker classes or by cross-linkers of the following combinations of cross-linker classes: I, II, III, IV, I II, I III, I IV, I II III, I II IV, I III IV, II III IV, II IV, or III IV. The above combinations of cross-linker classes represent a preferred embodiment of cross-linkers of a water-absorbing polymer particle.

Further embodiments of the polymers are polymers that are cross-linked by any of the above named cross-linkers of cross-linker class I. Among these, water-soluble cross-linkers are an aspect. In this context, N,N'-methylenebisacrylamide, polyethylene glycol di(meth)acrylates, triallylmethylammonium chloride, tetraallylammonium chloride, as well as allylnonaethylene glycol acrylate made with 9 mol ethylene oxide per mol acrylic acid are another aspect.

Water-soluble polymers ($\alpha 4$) such as partially or fully saponified polyvinyl alcohol, polyvinylpyrrolidone, starches or starch derivatives, polyglycols or polyacrylic acids can be comprised in, and in one aspect polymerized into, the water-absorbing polymer particles. The molecular weight of these polymers is not critical, as long as they are water-soluble. Water-soluble polymers can be starches or starch derivatives or polyvinyl alcohol. The water-soluble polymers, such as synthetic-like polyvinyl alcohol, can also serve as graft basis for the monomers to be polymerized.

Additives ($\alpha 5$), suspension agents, odor binders, surface-active agents, or antioxidants can be comprised in the water-absorbing polymer particles.

The above-described polymer particles comprising part of the powdery water-absorbing polymers according to the present invention can be produced by bulk polymerization that occurs in one aspect in kneading reactors such as extruders or by belt polymerization, solution polymerization, spray polymerization, inverse emulsion polymerization, and inverse suspension polymerization. Solution polymerization can be carried out in water as a solvent. The solution polymerization can occur continuously or discontinuously. The solution polymerization can occur as continuously running band polymerization. From the art, a broad spectrum of variation possibilities can be learned with respect to reaction proportions such as temperatures, type, and quantity of the initiators as well as of the reaction solution. Typical processes are described in the following patent specifications: U.S. Pat. No. 4,286,082, DE 27 06 135, U.S. Pat. No. 4,076,663, DE 35 03 458, DE 40 20 780, DE 42 44 548, DE 43 23 001, DE 43 33 056, and DE 44 18 818.

In order to convert the water-absorbing polymers obtained by the above-cited polymerization processes into a particulate form with an average particle size of at least about 100 μm in one aspect, in another aspect of less than about 150 μm, and in yet another aspect of less than about 200 μm, after their separation from the reaction mixture, these polymers can first be dried at a temperature in a range of about 20° C. to about 300° C. in one aspect, in another aspect within a range of about 50° C. to about 250° C., and in yet another aspect within a range from about 100° C. to about 200° C. to a water content of less than about 40 wt. % in one aspect, in another aspect of less than about 20 wt. %, and in yet another aspect of less than about 10 wt. %, based on the total weight of the polymer. The drying occurs in one aspect in ovens or driers known to those skilled in the art, for example in belt driers, drying hurdles ("Hordentrockner"), rotary kilns, fluid bed driers, disc driers, paddle driers, or infrared driers. Should the thus obtained, dried polymers not yet be present in particulate form, then they can be further comminuted after the drying. The comminuting can occur by dry-grinding in one aspect, and in another aspect by dry-grinding in a hammer mill, a pin mill, a ball mill, or a roll mill.

Besides the above-described process for transforming the polymers into a particulate form, the polymers can also be comminuted in the gel state by the process of wet grinding with any conventional device for wet grinding.

In a further embodiment, the water-absorbing polymer particles comprising part of the powdery water-absorbing polymer are based on biodegradable materials. Natural polysaccharides belong to this group, which already naturally comprise carboxyl groups or have been provided by subsequent modification with carboxyl groups. A first group of polysaccharides include for example starches, amylose, amylopectin, celluloses, and polygalactomannanes such as guar and locust bean gum, and a second group includes for example xanthane, alginates, and gum arabic.

In yet a further embodiment, the water-absorbing polymer particles comprising part of the powdery water-absorbing polymers are based on a mixture of biodegradable and synthetic water-absorbing polymer particles.

In even yet a further embodiment according to the present invention, the water-absorbing polymer particles comprise an inner portion, an outer portion surrounding the inner portion, and a surface portion surrounding the outer portion, whereby the outer portion has a higher degree of cross-linking than the inner portion, so that in one aspect a core-shell structure forms. The increased cross-linking in the surface portion of the powdery water-absorbing polymer can be achieved by means of secondary cross-linking of reactive groups near the surface. This secondary cross-linking can occur thermally, photochemically, or chemically. As secondary cross-linker for the chemical secondary cross-linking, compounds can be those that were mentioned as cross-linker ($\alpha 3$) of cross-linker classes II and IV. A secondary cross-linker can be ethylene carbonate.

In a process according to the present invention for producing powdery water-absorbing polymers, Steps can comprise bringing:

about 0.01 wt. % to about 20 wt. % in one aspect, in another aspect about 0.1 wt. % to about 15 wt. %, and in yet another aspect about 1 wt. % to about 10 wt. % of a fine particle which in one aspect is not based on water-absorbing cross-linked poly(meth)acrylates with an average particle size determined by sieve analysis of less than about 200 μm in one aspect, in another aspect of less than 100 μm, and in yet another aspect of less than about 50 μm;

about 0.001 wt. % to about 10 wt. % in one aspect, in another aspect about 0.01 wt. % to about 5 wt. %, and in yet another aspect about 0.5 wt. % to about 1 wt. % of a thermoplastic adhesive; and about 60 wt. % to about 99.998 wt. % in one aspect, in another aspect about 70 wt. % to about 99 wt. %, and in yet another aspect about 90 wt. % to about 95 wt. % of a water-absorbing polymer particle with an average particle size determined by sieve analysis of at least about 200 μm in one aspect, in another aspect of at least about 250 μm, and in yet another aspect of at least 300 μm, whereby the sum of the above components amounts to about 100 wt. %, into contact at a temperature within the range of about 120° C. to about 250° C. in one aspect, in another aspect about 150° C. to about 220° C., and in yet another aspect about 170° C. to about 200° C.

In an embodiment of the above process, a further component of at least one of the above-defined secondary cross-linkers is used. In this case, in one aspect, the water-absorbing fine particle is not secondary or surface cross-linked. In another aspect of this design, a thermoplastic adhesive and secondary cross-linker are used in a liquid phase, in one aspect in an aqueous solution, whereby the concentrations given above in the context of the liquid phase are also used. In this context, in one aspect, as a further component, a secondary cross-linker is brought into contact. In another aspect, the secondary cross-linker and the thermoplastic adhesive are added together to the other components, whereby at least the secondary cross-linker can be present in a liquid phase.

The water-absorbing polymer particles, thermoplastic adhesives, or fine particles that have already been mentioned in the context of the powdery water-absorbing polymers according to embodiments of the present invention can be used.

In one aspect, according to embodiments of the present invention, thermoplastic adhesives are used in particulate form in one aspect, and in another aspect in the form of a powder or of a granulate, whereby at least about 50 wt. % in one aspect, and in another aspect at least about 70 wt. % of the powder or the granulate has a particle size determined by sieve analysis within a range of about 1 μm to about 200 μm in one aspect, in another aspect within a range of about 10 μm to about 150 μm, and in yet another aspect within a range of about 20 μm to about 120 μm.

Should the thermoplastic adhesives mentioned in the context of the powdery water-absorbing polymers according to embodiments of the present invention not be present in particulate form after their production or their delivery, in particular for example if they are present in the form of blocks, these can be transformed by comminuting processes known to those skilled in the art, such as for example by grinding or by extruding through breaker plates and then comminuting the extruded particles into a particulate form with the necessary average particle size. Optionally, particular grinding processes can be used, for example cryogrinding at low temperatures, in particular at temperatures below the melt or glass transition temperature of the used thermoplastic adhesive. An aspect for the grinding to the desired particle size is the brittleness of the melt adhesive.

The bringing together of water-absorbing polymer particles, thermoplastic adhesives, and fine particles can occur in any suitable way. Aspects for the production of the powdery water-absorbing polymers according to embodiments of the present invention are, however, that at least a contact time between water-absorbing polymer particles, thermoplastic adhesive, and fine particle is complied with, which allows an adhesive binding mediated by the thermoplastic adhesive between at least one water-absorbing polymer particle and at least one fine particle. In one aspect, the contact time is measured so that aggregates are generated which are as small as possible, which ideally comprise only one water-absorbing polymer particle and one or more fine particle applied to the surface of the water-absorbing polymer particle by means of the thermoplastic adhesive. In one aspect, it should be avoided that agglomerates consisting of several water-absorbing polymer particles should form by the adhesive effect of the thermoplastic adhesive by contact times which are too long.

The bringing together of the water-absorbing polymer particles, the thermoplastic adhesive, and the fine particles can occur in any way according to a process according to embodiments of the present invention. Thus, for example the thermoplastic adhesives in particulate form as well as the fine particles, can already be brought into contact with the water-absorbing polymer particles during the production process for the water-absorbing polymer particles. For this purpose, it is for example suitable to contact the water-absorbing polymer particles with thermoplastic adhesive particles and the fine particles during a secondary cross-linking of the water-absorbing polymer particles, as is often carried out in the production of superabsorbent polymers.

With respect to the order of bringing into contact the individual components, different ways of proceeding are possible.

In an embodiment of the process according to the present invention, first the water-absorbing polymer particles are mixed with the particulate thermoplastic adhesive in the solid state. The water-absorbing polymer particles brought into contact with the thermoplastic adhesive in this way can then be mixed with the fine particles. In order to effect an adhesion, mediated by the thermoplastic adhesive, of the fine particles to the surface of the water-absorbing polymer fine particles, the thermoplastic adhesive is first be heated by means of a temperature increase to a temperature above the melt or glass transition temperature, so that it has a sticky behavior. The heating can occur to a time at which the water-absorbing polymer particles have been brought into contact with the thermoplastic adhesive but not yet with the fine particles. In this case, the mixture of the polymer fine particles and the thermoplastic adhesive is correspondingly heated to a temperature above the melt temperature of the thermoplastic adhesive, and this mixture is then brought into contact with the fine particles. In order to prevent an undesired agglomeration of the water-absorbing polymer particles, it can be advantageous to cool temporarily the polymer particles that have been brought into contact with the adhesive to a temperature below the melt temperature of the thermoplastic adhesive. During this cooling phase, the water-absorbing polymer particles are kept moving. A movement of this type can be caused for example by stirring, shaking, or flowing, or the like. After the bringing into contact the water-absorbing polymer particles coated with the thermoplastic adhesive with the fine particles, the temperature is increased again to a temperature above the melt or glass transition temperature of the thermoplastic adhesive, in order to ensure an adhesion between the water-absorbing polymer particles and the fine particles. In addition, in another embodiment of a process according to the present invention, the water-absorbing polymer particles can be first mixed with the fine particles, and then the thermoplastic adhesive can be added, followed by the warming in order to melt the thermoplastic adhesive. In this way, a more homogeneous mixture of the fine particles with the water-absorbing polymer particles can be achieved, which leads to less dust formation and an improved flowability.

It is however also possible to heat the thermoplastic adhesive for a time at which it has not yet been brought into contact with the water-absorbing polymer particles. In this case, first the thermoplastic adhesive is heated to a temperature above the melt or glass transition temperature of the thermoplastic adhesive and then brought into contact with the water-absorbing polymer particles. The water-absorbing polymer particles brought into contact with the thermoplastic adhesive in this way are then mixed with the fine particles, whereby a temporary cooling to prevent formation of larger agglomerates can also occur here.

In a further embodiment of a process according to the present invention, it is proceeded as above, with the difference that first the fine particles are mixed with the particulate thermoplastic adhesive in solid form and then the fine particles which have been brought into contact with the thermoplastic adhesive are mixed with the water-absorbing polymer particles.

In another embodiment of a process according to the present invention, however, the fine particles, the water-absorbing polymer particles, and the thermoplastic adhesive are brought together into contact at the same time. Thus, the thermoplastic adhesive in particulate form can be mixed with the water-absorbing polymer particles and the fine particles at a temperature below the melt temperature and the thus-obtained mixture then heated to a temperature above the melt temperature of the thermoplastic adhesive, in order to ensure the adhesion by the thermoplastic adhesive between the fine particles and the water-absorbing polymer particles. It is also possible first to heat the thermoplastic adhesive to a temperature above the melt temperature and to mix the thus-heated thermoplastic adhesive together with the fine particles and the water-absorbing polymer particles. Also in this embodiment of a process according to the present invention, in order to prevent an undesired agglomeration of the water-absorbing polymer particles, the polymer particles brought into contact with the adhesive may be temporarily cooled to a temperature below the melt or glass transition temperature of the thermoplastic adhesive. During this cooling phase, the water-absorbing polymer particles should be moved.

The contact of the water-absorbing polymer particles with the thermoplastic adhesive and the fine particles can occur in mixing aggregates known to those skilled in the art. Suitable mixing aggregate components are, e.g., the Patterson-Kelley mixer, DRAIS turbulence mixer, Lödige mixer, Ruberg mixer, screw mixer, plate mixer, and fluidized bed mixer as well as continuously-conveying, such as vertical mix ovens, in which the particles are mixed with a rapid frequency by means of rotating knives and which have movable, heated conveying means.

In one aspect according to the present invention, powdery water-absorbing polymers are secondary cross-linked in the surface portion in a further process step, whereby those secondary cross-linkers can be those which have already been mentioned in the context of powdery water-absorbing polymers according to embodiments of the present invention as secondary cross-linkers.

There are various possibilities for the timing of the secondary cross-linking during the process according to an embodiment of the present invention.

In one embodiment of a process according to the present invention, the secondary cross-linking occurs before the water-absorbing polymer particles have been brought into contact with the thermoplastic adhesive and the fine particles. In this case, the polymer fine particles are brought into contact with the secondary cross-linker, in one aspect with a fluid comprising a solvent, such as water, organic solvents such as methanol, ethanol, 1-propanol, or 2-propanol, or a mixture of at least two thereof, and the secondary cross-linker. The water-absorbing polymer particles which have been brought into contact with the secondary cross-linker are then heated to a temperature within a range of about 50° C. to about 300° C. in one aspect, in another aspect within a range of about 100° C. to about 250° C., and in yet another aspect within a range of about 150° C. to about 200° C., in order to carry out the secondary cross-linking. The thus secondary cross-linked polymer particles are then brought into contact as described above with the thermoplastic adhesive and the fine particles.

In another embodiment of a process according to the present invention, the secondary cross-linking is carried out after the water-absorbing polymer particles have been brought into contact with the thermoplastic adhesive and the fine particles. In this case, the powdery water-absorbing polymers, in whose surface portion the fine particles are immobilized by means of the thermoplastic adhesive, are secondary cross-linked in the above-described type and way.

In an embodiment of a process according to the present invention, the secondary cross-linking occurs during the bringing into contact of the water-absorbing polymer particles with the thermoplastic adhesive and the fine particles. In another embodiment according to the present invention, the water-absorbing polymer particles with the particulate thermoplastic adhesive, the fine particles, and the secondary cross-linker, in one aspect with the secondary cross-linker in the form of a fluid comprising the secondary cross-linker and a solvent, is mixed and then heated to a temperature above the melt temperature.

In one aspect, the secondary cross-linker is used in a quantity within a range of about 0.01 wt. % to about 5 wt. %, in another aspect within a range of about 0.3 wt. % to about 3 wt. %, and in yet another aspect in a quantity within a range of about 0.5 wt. % to about 1.5 wt. %, based on the weight of the water-absorbing polymer particles. If the secondary cross-linker is used in the form of a fluid, in one aspect in the form of an aqueous solution or dispersion, this fluid comprises the secondary cross-linker in one aspect in a quantity within a range of about 10 wt. % to about 80 wt. %, in another aspect in a quantity within a range of about 30 wt. % to about 70 wt. %, and in yet another aspect in a quantity within a range of about 40 wt. % to about 50 wt. %, based on the total weight of the fluid.

Embodiments of the present invention also relate to the powdery water-absorbing polymers obtainable by the above-described processes, whereby these powdery water-absorbing polymers in one aspect have the same properties as the powdery water-absorbing polymers according to an embodiment of the present invention as described previously.

In another aspect, the powdery water-absorbing polymers obtainable by a process according to embodiments of the present invention are characterized by:

P1 A flow value (FFC) within the range of about 1 to about 13 in one aspect, in another aspect within the range of about 3 to about 9, and in yet another aspect within the range of about 4 to about 8, and in even yet another aspect within the range of about 5 to about 7; or P2 A dust portion of at most about 6 in one aspect, in another aspect at most about 4, and in yet another aspect at most about 2.

In another aspect according to embodiments of the present invention, the powdery water-absorbing polymers according to embodiments of the present invention and the powdery water-absorbing polymers obtainable by a process according embodiments of to the present invention have in one aspect at least one, and in another aspect all of the following properties:

P3 An attrition index $A_i$ within the range of about 1 to about 17 in one aspect, in another aspect within the range of about 1.1 to about 15, and in another aspect within the range of about 1.5 to about 10;

P4: An attrition difference $A_d$ within the range of 0 to about 7 in one aspect, in another aspect within the range of about 1.1 to about 6, and in yet another aspect within the range of about 1.5 to about 3; and P5: A retention determined according to ERT 441.1-99 of at least about 20 g/g in one aspect, in another aspect at least about 25 g/g, and in yet another aspect at least about 27 g/g, as well as in even yet another aspect within the range of about 27 to about 35 g/g.

The property combinations arising from two or more of the above properties P1 to P5 of represent embodiments of the present invention. In another aspect, the powdery water-absorbing polymers according to embodiments of the present invention have the following properties or property combinations represented as follows by letters or combinations of letters: P1P3P4P5, P1P5, P1P3P5, P3P5, or P1P2P3P4P5.

Embodiments of the present invention relate to a powdery water-absorbing polymer comprising at least about 30 wt. % in one aspect, in another aspect at least about 75 wt. %, and in another aspect at least about 95 wt. % a cross-linked, partially neutralized, in one aspect neutralized within the range of about 60 mol.% to about 80 mol.%, polyacrylic acid and with at least one in one aspect, and in another aspect all of the properties P1 to P5, in one aspect the property combinations P1P3P4P5, P1P5, P1P3P5, and in another aspect the property combination P3P5.

In another aspect, at least about 50 wt. % in one aspect, in another aspect at least about 70 wt. %, and in yet another aspect at least about 90 wt. % of the powdery water-absorbing polymers obtainable by a process according to embodiments of the present invention as well as the powdery water-absorbing polymers according to embodiments of the present invention have a particle size determined by sieve analysis within the range of greater than about 50 μm to about 2,000 μm in one aspect, in another aspect in a range of about 100 μm to about 1,500 μm, and in yet another aspect in a range of about 200 μm to about 1,200 μm.

In a transport process according to embodiments of the present invention, the powdery water-absorbing polymers obtainable by a process according to embodiments of the present invention or the powdery water-absorbing polymers according to embodiments of the present invention flow through a pipe, whereby the pipe in one aspect forms a part of an installation for producing a water-absorbing polymer or of a dosing system for a water-absorbing polymer. Dosing systems of this type can, for example, be used in charging containers or bags or are situated in airlaid machines or diaper machines. In another aspect, the pipe is the pipe in which the powdery water-absorbing polymers are conducted when they are brought into contact with a fibrous material, such as for example cotton fibers, to form an absorbent core or nucleus ("Kern").

The composite according to an embodiment of the present invention comprises an above-defined powdery water-absorbing polymer and a substrate. In one aspect, a powdery water-absorbing polymer according to embodiments of the present invention and the substrate are bonded together. As substrates, layers made from polymers, such as for example polyethylene, polypropylene or polyamide, metals, non-woven materials, fluff, tissues, webs, natural or synthetic fibers or other foams are one aspect.

A composite according to embodiments of the present invention can be sealant materials, cables, absorbent cores, as well as diapers and hygiene articles comprising these.

In a process according to embodiments of the present invention for producing a composite, a powdery water-absorbing polymer according to embodiments of the present invention, or a powdery water absorbent polymer obtainable by a process according to embodiments of the present invention, a substrate and optionally a suitable auxiliary are brought into contact with each other. In one aspect, the bringing into contact occurs by wetlaid processes and airlaid processes, compacting, extruding, and mixing.

The invention additionally relates to a composite that is obtainable by the above process.

Embodiments of the present invention further relate to chemical products, in particular foams, formed bodies, fibers, sheets, films, cables, sealant materials, liquid-absorbing hygiene articles, carriers for plant or fungus growth regulating agents or plant protection active substances, additives for building materials, packaging materials or soil additives, which comprise the powdery water-absorbing polymer according to embodiments of the present invention, or the powdery water-absorbing polymer obtainable by a process according to embodiments of the present invention or the above-described composite.

The chemical products are characterized in particular by a particularly good biodegradability.

In addition, embodiments of the present invention relate to the use of the powdery water-absorbing polymer according to embodiments of the present invention or the powdery water-absorbing polymer obtainable by a process according to embodiments of the present invention or of the above-described composite in hygiene products, in fighting floods, in insulation against water, in regulation of the water management in soil, or in treating food products.

Finally, embodiments of the present invention also relate to the use of a thermoplastic adhesive for alteration of the flow value (FFC) or of the dust portion in powdery water-absorbing polymers comprising this thermoplastic adhesive with respect to powdery water-absorbing polymers that do not comprise this thermoplastic adhesive, whereby as thermoplastic adhesive, those adhesives can be those which have already been mentioned in the context of the powdery water-absorbing adhesives according to embodiments of the present invention.

Embodiments of the present invention are now more closely described by means of test methods and non-limiting examples.

Test Methods

Determination of the FFC Value

The FFC value gives information regarding the flow properties of a bulk material in a silo. In the measurement, the bulk material is subjected to different stresses. The flow behavior can be characterized as follows;

| | |
|---|---|
| FFC < 1 | non-flowing |
| 1 < FFC < 2 | very cohesive |
| 2 < FFC < 4 | cohesive |
| 4 < FFC < 10 | slightly flowing |
| 10 < FFC | free flowing |

A good flow behavior is present if a bulk material can be made to flow without great effort, e.g., if the bulk material runs out of a funnel or of a silo without consolidation. With poorly flowing bulk materials, disruptions of the running out occur or they consolidate during transport or storage. The term "to flow" is meant that the bulk material deforms in a plastic manner because of stress.

Further details regarding how to conduct tests for a determination of FFC can be found in the articles from Dr. Ing. Ditmar Schulze "Das automatische Ringschwergerät RST-01.pc" from February 2002 and "Fliesseigenschaften von Schüttgütern und verfahrenstechnische Siloauslegung" from the year 2002. In the present measurements, the manually operated variant of the circular shear apparatus RST-01.01 is used.

Determination of the Dust Portion

The dust portion is determined with an apparatus of the company Palas, Germany of the type "Dust View." To this end, a sample of 30.00 g is placed in a funnel pipe. At the start of the measurement, the funnel flap opens automatically and the sample falls into a dust reservoir. The reduction of a laser beam (reduction of the transmission) is measured by the dust formation. This value serves for the determination of the dust portion, i.e., the cloudiness, in percent with a scale from 1 to 100. The dust portion is given by a start value at the start of the measurement and a dust value measured after 30 seconds for determining the floating portion. Thus, the dust portion is given by the sum of the start value and the dust value.

Determination of the Attrition Index and the Attrition Difference

Figure 1:
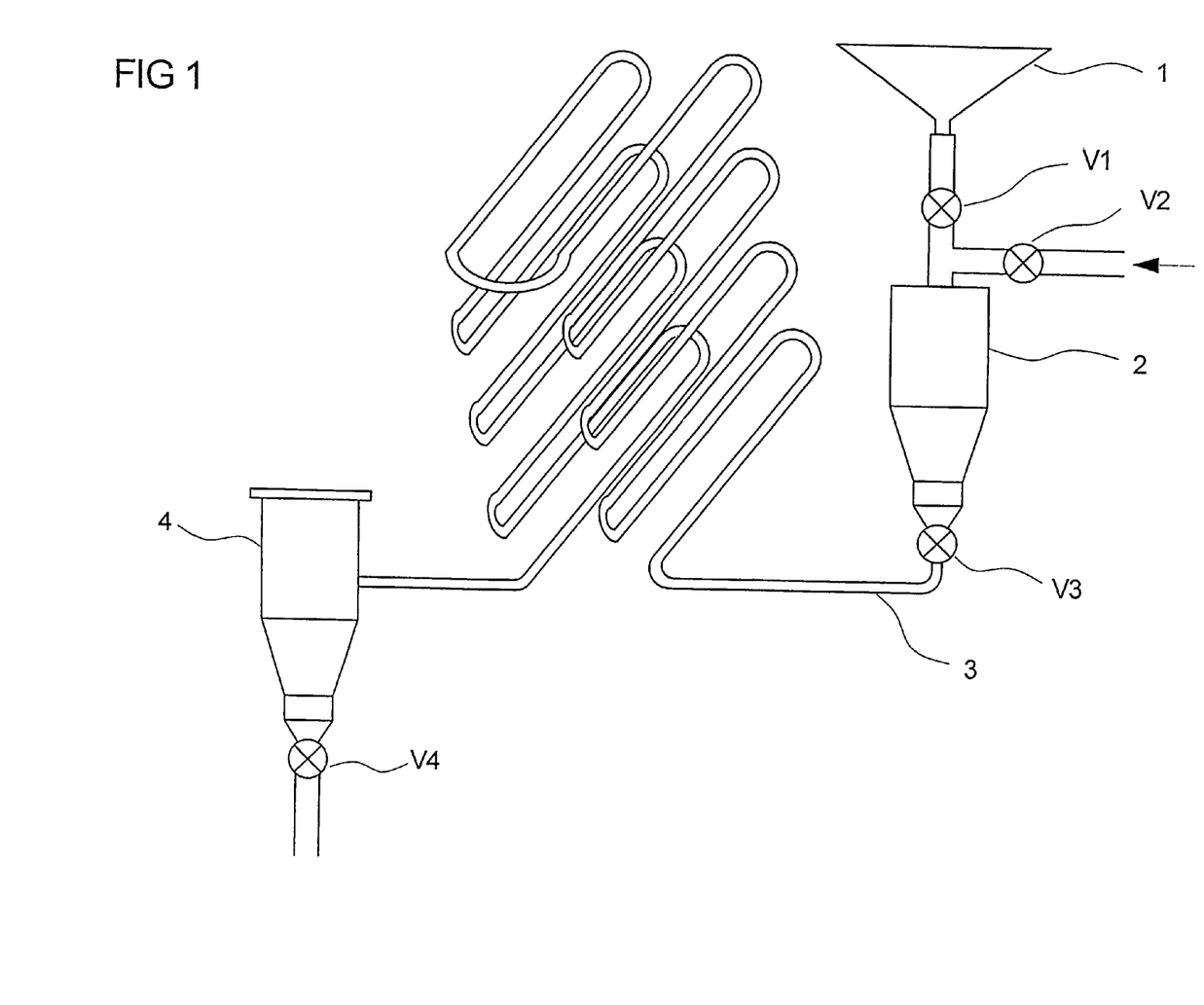
FIG. 1 is a schematic showing a funnel for introducing a sample into a probe chamber.

The test device represented in FIG. 1 is used for this purpose. This consists of a funnel 1 for introducing a sample into a probe chamber 2. Between the funnel and the probe absorption chamber 2, a conduit is provided, with a charging valve V1 and a feed line provided with a gas regulating valve V2 arranged under charging valve V1. By means of V2, a pressure of 4.3 bar is applied to the sample absorption chamber 2. This consists of a cylinder with a diameter of 9 cm and a length of 16 cm. A blunt cone-shaped lower region is attached to this cylinder, said lower region having a lower opening with a diameter of 4 cm. To this is attached a 2 cm long pipe with a diameter of 4 cm, which leads intern to a further blunt cone-shaped cycle with a length of 4.5 cm and a lower diameter of 1.75 cm. To this is attached a chamber outlet valve V3. From V3, a pipe-conduit with an inner diameter of 10 mm and a total length of 1101 cm follows via a curved piece of 90 degrees and of 4.5 cm length. The pipe conduit begins with a straight section of 30 cm, followed by 16 straight sections each with a length of 60 cm linked with curved piece of 90 degrees and of 4.5 cm length, the 16 straight sections being joined together via 180 degrees curved sections of respectively 4.5 cm. To the 16 sections is attached a further straight section of 30 cm length via a curved piece of 90 degrees and 4.5 cm length. This section leads into a sample collection chamber 4, which only differs in its construction from chamber 2 in that instead of the upper cover, a filter bag with a substantially smaller pore size in comparison to the particle size of the samples is applied. The sample collection chamber is sealed below by a sample removal valve V4. All metal parts of the above-described test device are made from 316 alloy stainless steal. The tubes are standard stock pipes. The inner surfaces of the individual components of the device are smooth. Valves of the type 20 SS0R-02-LL-9102 from the company Milwaukee Valve Company, USA were used.

The above-described device is operated as follows:

Step 1-Sample Charging

The valves V1 and V4 are open, valves V2 and V3 are closed. 50 g of a sample is loaded into chamber 2 using funnel 1.

Step 2-Sample transport

The valves are activated in the following order: a) V1 closed, b) V2 opened, c) V3 closed. After the pipe shows no more oscillation caused by passage of the sample, the following valve positions are set: a) V2 closed, V1 open, V3 closed.

Step 3-Sample removal

To remove the sample, a vessel is placed under V4, and by carefully opening V4, the sample is loaded into the vessel for further investigation. V4 is then closed again.

The sample is subjected to the determination according to DIN 55992-2 both before step 1 and after step 3 for the determination of the dust portion before ($S_{vorA}$) and after attrition ($S_{nachA}$).

The "attrition index "A" is given by $A_j=S_{afterA}/S_{beforeA}$.

The "attrition difference" Ad is given by $A_d=S_{afterA}-S_{beforeA}$.

EXAMPLES

In the following examples a particulate, lightly cross-linked, partially neutralized polyacrylic acid is used as pre-product, which is commercially obtainable from the company Stockhausen GmbH & Co. KG under the trade name FAVOR® of the type Z3050. This has a retention of 33 g/g and a dust portion of 3.7.

Example 1

Production of the powdery water-absorbing polymer according to an embodiment of the present invention:

1000 g of the pre-product were placed with the quantities given in table 1 of fine particles and thermoplastic adhesive in a vertical mixer (MTI-Mischtechnik Industrieanlagen GmbH, type LM 1.5/5) and combined at 750 rpm with 40 g 25 wt. % ethylene carbonate solution.

The coated pre-product was transferred to a Gericke powder conveyor (Gericke GmbH, type GLD 75) and conveyed continuously with a conveyor performance of 20 g/min into a Labor-Nara-reactor (HTM Reetz GmbH, type Laboratory paddle mixer "Mini-Nara II"). The dwell time in the dryer was approximately 90 minutes and the product was heated to a maximum temperature of 185° C. to 195° C. During this time, the secondary cross-linking occurred and the thermoplastic adhesive was melted, influenced the flow behavior, distributed itself on the surface and bound the fine particles to the surface of the water-absorbing polymer particles.

TABLE 1

| Experiment number | Fine particles | Quantity of fine particles | Thermoplastic adhesive | Quantity of thermoplastic adhesive | FFC | Dust portion |
|---|---|---|---|---|---|---|
| 1 (HBr 7/127) | Mg HPO$_4$ 3 H$_2$O (<50 μm) | 1.0 wt. % | SchaettiFix ® 386[1] | 0.5 wt. % | 5.4 | 0.2 |
| 2 (HBr 7/128) | Technocell ® 75 (cellulose fiber <75 μm) | 1.0 wt. % | SchaettiFix ® 386[1] | 0.5 wt. % | 4.3 | 0.1 |

[1]Product of the company Schaetti AG, Zurich, Switzerland; melting range: 130 to 160° C., melt viscosity at 160° C.: 520 Pas, thermal stability: 120° C.

Example 2

The results collected in table 2 were produced as described in example 1 with the materials and quantities given in table 2 and 60 g of the 25 wt. % ethylene carbonate solution. The samples were subjected to the attrition test. The FFC value was determined after carrying out the attrition test. The CRC value was determined before and after carrying out the attrition test.

TABLE 2

|  | Control | Vestamelt ®[2] 4481 | SchaettiFix ® 386 |
|---|---|---|---|
|  |  | Experiment number |  |
|  | 3 | 4 | 5 |
| Quantity of thermoplastic adhesive | — | 0.3 wt. % | 0.3 wt. % |
| Dust portion[3] $S_{beforeA}$ | 0.44 | 0.40 | 0.39 |
| Dust portion[3] $S_{afterA}$ | 7.53 | 3.48 | 3.05 |
| $A_f$ | 17.11 | 8.7 | 8.97 |
| $A_d$ | 7.09 | 3.08 | 2.66 |
| FFC before attrition test | 8.7 | 4.6 | 5.0 |
| CRC value before attrition test [g/g] | 27.3 | 27.5 | 27.2 |

[2] product of Degussa AG, Düsseldorf, Germany
[3] quadruple determination

Example 3

Production of a powdery water-absorbing polymer by coating with a thermoplastic adhesive in the presence of superabsorbent polymer fine particles;

1000 g of the pre-product was placed with the quantities given in table 3 of thermoplastic adhesive in a vertical mixer (MTI-Mischtechnik Industrieanlagen GmbH; type LM 1.5/5) and coated at 750 rpm with 40 g 25 wt. % ethylene carbonate solution.

The coated pre-product was transferred into a Gericke powder conveyor (Gericke GmbH, type GLD 75) and conveyed continuously with a conveyor performance of 20 g/min into a Labor-Nara reactor (HTM Reetz GmbH, type laboratory paddle mixer "Mini-Nara II"). The dwell time in the dryer was approximately 90 minutes and the product was heated to a maximum temperature of 185° C. to 195° C. During this time, the secondary cross-linking occurred and the thermoplastic adhesive was melted, influenced the flow behavior and distributed itself on the surface.

TABLE 3

| Experiment number | Fine particles | Quantity of fine particles | Thermoplastic adhesive | Quantity of thermoplastic adhesive | FFC | Dust portion |
|---|---|---|---|---|---|---|
| 6 (HBr 7/126) | — | — | SchaettiFix ® 386 | 0.5 wt. % | 5.1 | 0.4 |
| 7 control (HBr 7/125) | — | — | — | — | — | 4.5 |

The examples show that by the use of thermoplastic adhesives, both the superabsorbent polymer fine particles that accompany the water-absorbing polymer and also further fine particles that are different from the water-absorbing polymer can be bound to water-absorbing polymer particles with high stability and reduction of the dust portion, without the absorption properties such as retention of the thus-obtained water-absorbing polymer particles, or flowability, suffering.

The invention claimed is:

1. Treated water-absorbing polymer particles comprising:
   from about 0.01 to about 20 percent by weight of the polymer of a fine particle with a particle size of less than about 200 μm;
   from about 0.001 to less than 0.3 percent by weight of the polymer of a thermoplastic adhesive; and
   from about 60 to about 99.998 percent by weight of the polymer of a water-absorbing polymer particle with a particle size of about 200 μm and above, wherein
   wherein the treated water-absorbing polymer particles are prepared by a production process and the fine particles are bound to the surface of the water-absorbing polymer particles by the thermoplastic adhesive during the production process for the treated water-absorbing polymer particles, and the treated water-absorbing polymer particles have either
   a flow value (FFC) comprising from about 1 to about 13 according to the Determination of the FFC Value set forth in the present application, or
   a dust portion comprising at most about 6 according to the Determination of the Dust Portion method set forth in the present application.

2. The treated water-absorbing polymer particles according to claim 1, wherein the flow value (FFC) comprises from about 1 to about 13 and the dust portion comprises at most about 6, respectively based on the total weight of the powdery water-absorbing polymers.

3. The treated water-absorbing polymer particles according to claim 1, wherein the thermoplastic adhesive has a melt temperature according to ISO 11357 of at least about 50° C.

4. The treated water-absorbing polymer particles according to claim 1, wherein the thermoplastic adhesive has a melt viscosity according to Brookfield (ASTM E 28) with a number 27 spindle at a temperature of about 160° C. and less than about 2000 Pas.

5. The treated water-absorbing polymer particles according to claim 1, wherein the thermoplastic adhesive comprises at least about 10 percent by weight of the adhesive of a polycondensate.

6. The treated water-absorbing polymer particles according to claim 5, wherein the polycondensate comprises a polyester.

7. The treated water-absorbing polymer particles according to claim 1, wherein at least about 80 percent by weight of the fine particle comprises an inorganic fine particle.

8. The treated water-absorbing polymer particles according to claim 1, wherein the water-absorbing polymers include secondary crosslinking in a surface region.

9. The treated water-absorbing polymer particles according to claim 8, wherein the surface crosslinking in the surface region comprises crosslinking effected by at least one organic compound or at least one polyvalent metal cation.

10. Treated water-absorbing particles obtainable by a process comprising the steps of:
   providing from about 0.01 to about 20 percent by weight of a fine particle with a particle size of less than about 200 μm;
   providing from about 0.001 to about 0.3 percent by weight of a thermoplastic adhesive;
   providing from about 60 to about 99.998 percent by weight of a water-absorbing polymer particle with a particle size of about 200 μm and above; and
   wherein the treated water-absorbing polymer particles are prepared by a production process, and contacting the fine particle, the thermoplastic adhesive, and the water-absorbing polymer particle with each other at a temperature comprising from about 120 to about 250° C. during the production process for the treated water-absorbing polymer particles.

11. The treated water-absorbing polymer particles according to claim 10 comprising at least one of the following properties:
   P1 a flow value (FFC) comprising from about 1 to about 13; or
   P2 a dust portion comprising at most about 6,
   P3 an attrition index $A_i$, comprising from about 1 to about 17;
   P4 an attrition difference $A_d$ comprising from 0 to about 7; or
   P5 a retention determined according to ERT 441.1-99 comprising at least about 20 g/g.

12. The treated water-absorbing polymer particles according to claim 1, wherein at least about 50 percent by weight of the powdery water-absorbing polymers have a particle size comprising from about 50 to about 2,000 μm.

13. A composite comprising the treated water-absorbing polymer particles according to claim 1.

14. A chemical product comprising the treated water-absorbing polymer particles according to claim 1.

15. The treated water-absorbing polymer particles according to claim 8, wherein the water-absorbing polymer particles are contacted with the thermoplastic adhesive and the fine particles during a secondary cross-linking of the water-absorbing polymer particles.

16. A process for producing treated water-absorbing polymer particles comprising the steps of:
   providing from about 0.01 to about 20 percent by weight of a fine particle with a particle size of less than about 200 μm;
   providing from about 0.001 to less than 0.3 percent by weight of a thermoplastic adhesive;
   providing from about 60 to about 99.998 percent by weight of a water-absorbing polymer particle with a particle size of about 200 μm and above; and
   contacting the fine particle, the thermoplastic adhesive, and the water-absorbing polymer particle with each other at a temperature comprising from about 120 to about 250° C.
   wherein the treated water-absorbing polymer particles have either
      a flow value (FFC) comprising from about 1 to about 13 according to the Determination of the FFC Value set forth in the present application, or
      a dust portion comprising at most about 6 according to the Determination of the Dust Portion method set forth in the present application.

17. The process for producing treated water-absorbing polymer particles according to claim 16, wherein the contacting occurs in a continuously conveying mixing oven.

18. The process for producing treated water-absorbing polymer particles according to claim 17 wherein the oven comprises movable, heated conveying means.

19. The process for producing treated water-absorbing polymer particles according to claim 16 further comprising providing a secondary crosslinker and contacting the secondary crosslinker with any one of the fine particle, the thermoplastic adhesive, the water-absorbing polymer particle, or any combination of any of the preceding.

20. The process for producing treated water-absorbing polymer particles according to claim 19 wherein the contacting comprises contacting the secondary crosslinker and the thermoplastic adhesive with the fine particle and the water-absorbing polymer particle.

21. The process for producing treated water-absorbing polymer particles according to claim 19 wherein at least the secondary crosslinker comprises a liquid phase.

22. The treated water-absorbing polymer particles according to claim 1, wherein the flow value (FFC) or dust portion in said powdery water-absorbing polymer is altered by the process comprising adding a thermoplastic adhesive to the powdery water-absorbing polymer.

23. The treated water-absorbing polymer particles according to claim 1, wherein said treated water-absorbing polymer particles are transported according to a transport process comprising flowing the treated water-absorbing polymer particles according to claim 1 through a channel.

24. The treated water-absorbing polymer particles according to claim 1, wherein the flow value (FFC) or dust portion in said powdery water-absorbing polymer is altered by a process comprising adding a thermoplastic adhesive to the powdery water-absorbing polymer.

* * * * *